(12) United States Patent
Huang et al.

(10) Patent No.: US 7,424,368 B2
(45) Date of Patent: Sep. 9, 2008

(54) METHODS FOR IDENTIFYING DNA COPY NUMBER CHANGES

(75) Inventors: Jing Huang, Sunnyvale, CA (US); Keith W Jones, Sunnyvale, CA (US); Michael H. Shapero, Redwood City, CA (US)

(73) Assignee: Affymetix, Inc., Santa Clara, CA (US)

( * ) Notice: Subject to any disclaimer, the term of this patent is extended or adjusted under 35 U.S.C. 154(b) by 454 days.

(21) Appl. No.: 10/712,616

(22) Filed: Nov. 12, 2003

(65) Prior Publication Data

US 2004/0157243 A1 Aug. 12, 2004

Related U.S. Application Data

(60) Provisional application No. 60/467,105, filed on Apr. 30, 2003, provisional application No. 60/319,685, filed on Nov. 11, 2002, provisional application No. 60/319,750, filed on Dec. 3, 2002.

(51) Int. Cl.
*G06F 19/00* (2006.01)
*G01N 33/48* (2006.01)

(52) U.S. Cl. ............... 702/19; 703/2; 435/6; 536/25.4; 211/41.12

(58) Field of Classification Search .................. None
See application file for complete search history.

(56) References Cited

U.S. PATENT DOCUMENTS

| | | | |
|---|---|---|---|
| 5,665,549 | A | 9/1997 | Pinkel et al. |
| 5,856,097 | A | 1/1999 | Pinkel et al. |
| 5,965,362 | A | 10/1999 | Pinkel et al. |
| 5,976,790 | A | 11/1999 | Pinkel et al. |
| 6,180,349 | B1 | 1/2001 | Ginzinger et al. |
| 6,268,142 | B1 | 7/2001 | Duff |
| 6,309,822 | B1 | 10/2001 | Fodor et al. |
| 6,326,148 | B1 | 12/2001 | Pauletti et al. |
| 6,335,167 | B1 | 1/2002 | Pinkel et al. |
| 6,432,648 | B1 | 8/2002 | Blumenfeld |
| 6,455,258 | B2 | 9/2002 | Bastian et al. |
| 6,455,280 | B1 | 9/2002 | Edwards |
| 6,468,744 | B1 | 10/2002 | Cronin et al. |
| 2001/0034043 | A1 | 10/2001 | Stanton |
| 2002/0165345 | A1 | 11/2002 | Conen |

FOREIGN PATENT DOCUMENTS

WO   WO 99/23256   5/1999

OTHER PUBLICATIONS

Zhou et al. (BMC Bioinformatics, vol. 3, Jan. 2002).*
Draghici (Drug Discovery Today, vol. 7, pp. S55-63, Jun. 2002).*
Kaminski et al. (American Journal of Respiratory Cell and Molecular Biology, vol. 27, pp. 125-132, Aug. 2002).*
Wodicka et al., (Nature Biotechnology, 15, 1359-1367, 1997).*
Buckley et al., A Full-coverage, High-resolution Human Chromosome 22 Genomic Mircroarray for Clinical and Research Applications, Human Molecular Genetics, 2002, 3221-3229, vol. 11(5).
Dumur et al., Genome-wide Detection of LOH in Prostate Cancer using Human SNP Microarray Technology. Genomics, 2003, 260-269, vol. 81.
Kallioniemi et al., Comparative Genomic Hybridization: A Powerful New Method for Cytogenetic Analysis of Solid Tumors. Science, 1992, 818-821, vol. 258.
Kennedy et al., Large-scale Genotyping of Complex DNA. Nature Biotechnology, Oct. 2003, 1233-1237, vol. 21 (10).
Klein et al., Comparative Genomic Hybridization, Loss of Heterozygosity, and DNA Sequence Analysis of Single Cells, Proc Natl Acad Sci, 1999, 4494-4499, vol. 96.
Lindblad-Toh et al., Loss of Heterozygosity Analysis of Small Cell Lung Carcinomas Using Single-Nucleotide Polymorphism Arrays. Nature Biotechnology, Sep. 2000, 1001-1005, vol. 18.
Lucito et al., Representational Oligonucleotide Microarray Analysis: A High-Resolution Method to Detect Genome Copy Number Variation. Genome Research, 2003, 2291-2305, vol. 13 (1D).
Lucito et al., Detecting Gene Copy Number Fluctuations in Tumor Cells by Microarray Analysis of Genomic Representations. Genome Research, 2000, 1726-1736, vol. 10(11).
Lucito et al., Genetic Analysis Using Genomic Representations. Proc Natl Acad Sci, Apr. 1998, 4487-4492, vol. 95.
Mei et al., Genome-wide Detection of Allelic Imbalance Using Human SNPs and High-density DNA Arrays. Genome Research. 2000, 1126-1137, vol. 10 (8).
Pinkel et al., High-Resolution Analysis of DNA Copy Number Variation Using Comparative Genomic Hybridization to Microarrays. Nature Genetics, 1998, 207-211, vol. 20.
Pollack et al., Microarray Analysis Reveals a Major Direct Role of DNA Copy Number Alterations in the Transcriptional Program of Human Breast Tumors. Proc Natl Acad Sci, Oct. 2002, 12963-12968, vol. 99 (20).
Schubert et al., Single Nucleolide Polymorphism Array Analysis of Flow-Sorted Epithelial Cells from Frozen Versus Fixed Tissues for Whole Genome Analysis of Allelic Loss in Breast Cancer. Am J Pathol, 2002, 73-79, vol. 160.
Snijders et al., Assembly of Microarrays for Genome-wide Measurement of DNA Copy Number. Nature Genetics, 2001, 263-264, vol. 29.

* cited by examiner

*Primary Examiner*—Carolyn Smith
(74) *Attorney, Agent, or Firm*—Sandra E. Wells

(57) ABSTRACT

Methods of estimating genomic DNA copy number are disclosed. Amplified genomic DNA is hybridized to an array of allele specific SNP probes to generate a hybridization pattern. A value, S, is calculated for individual SNPs in the experimental sample, where S is the log of the arithmetic average of the intensities of the perfect match probes for the SNP. S is calculated for the SNP in reference samples that are matched to the experimental sample in genotype. The mean and standard deviation for the S values of the reference samples are calculated and a log intensity difference is calculated by subtracting the mean values for the reference and experimental samples. The copy number of the SNP region is estimated using the difference between the mean for the SNP in the reference samples and the S value for the SNP in the experimental sample in a log-log linear model.

23 Claims, 3 Drawing Sheets

3B

3A

METHODS FOR IDENTIFYING DNA COPY NUMBER CHANGES

RELATED APPLICATIONS

This application claims the priority of U.S. Provisional Application Nos. 60/467,105 filed Apr. 30, 2003, 60/319,685 filed Nov. 11, 2002 and 60/319,750 filed Dec. 3, 2002 the disclosures of which are incorporated herein by reference in their entireties.

FIELD OF THE INVENTION

The invention is related to methods of estimating the number of copies of a genomic region that are present in a sample. Specifically, this invention provides methods, computer software products and systems for the detection of regions of chromosomal amplification and deletion from a biological sample.

BACKGROUND OF THE INVENTION

The underlying progression of genetic events which transform a normal cell into a cancer cell is characterized by a shift from the diploid to anueploid state (Albertson et al. (2003), Nat Genet, Vol. 34, pp.369-76 and Lengauer et al. (1998), Nature, Vol. 396, pp.643-9). As a result of genomic instability, cancer cells accumulate both random and causal alterations at multiple levels from point mutations to whole-chromosome aberrations. DNA copy number changes include, but are not limited to, loss of heterozygosity (LOH) and homozygous deletions, which can result in the loss of tumor suppressor genes, and gene amplification events, which can result in cellular proto-oncogene activation. One of the continuing challenges to unraveling the complex karyotype of the tumor cell is the development of improved molecular methods that can globally catalogue LOH, gains, and losses with both high resolution and accuracy.

Numerous molecular approaches have been described to identify genome-wide LOH and copy number changes within tumors. Classical LOH studies designed to identify allelic loss using paired tumor and blood samples have made use of restriction fragment length polymorphisms (RFLP) and, more often, highly polymorphic microsatellite markers (STRS, VNTRs). The demonstration of Knudson's two-hit tumorigenesis model using LOH analysis of the retinoblastoma gene, Rb1, showed that the mutant allele copy number can vary from one to three copies as the result of biologically distinct second-hit mechanisms (Cavenee, et al. (1983), Nature, Vol. 305, pp.779-84.). Thus regions undergoing LOH do not necessarily contain DNA copy number changes. Approaches to measure genome wide increases or decreases in DNA copy number include comparative genomic hybridization (CGH) (Kallioniemi, et al. (1992), Science, Vol. 258, pp.818-21.), spectral karyotyping (SKY) (Schrock,et al. (1996), Science, Vol. 273, pp.494-7.), fluorescence in situ hybridization (FISH) (Pinkel et al. (1988), Proc Natl Acad Sci USA, Vol. 85, pp.9138-42), molecular subtraction such as RDA (Lisitsyn et al. (1995), Proc Natl Acad Sci USA, Vol. 92, pp.151-5.; Lucito et al. (1998), Proc Natl Acad Sci USA, Vol. 95, pp.4487-92), and digital karyotyping (Wang, et al.(2002), Proc Natl Acad Sci USA, Vol. 99, pp.16156-61.). CGH, perhaps the most widely used and powerful approach, uses a mixture of DNA from normal and tumor cells that has been differentially labeled with fluorescent dyes. Target DNA is competitively hybridized to metaphase chromosomes or, in array CGH, to cDNA clones (Pollack et al. (2002), Proc Natl Acad Sci USA, Vol. 99, pp.12963-8) or bacterial artificial chromosomes (BACs) and P1 artificial chromosomes (PACs) (Snijders et al. (2001), Nat Genet, Vol. 29, pp.263-4, Pinkel,et al. (1998), Nat Genet, Vol. 20, pp.207-11). Hybridization to metaphase chromosomes, however, limits the resolution to 10-20 Mb, precluding the detection of small gains and losses. While the use of arrayed cDNA clones allows analysis of transcriptionally active regions of the genome, the hybridization kinetics may not be as uniform as when using large genomic clones. Currently, the availability of BAC clones spanning the genome limits the resolution of CGH to 1-2 Mb, but the recent use of oligonucleotides improves resolution to 15 Kb (Lucitoet al. (2003), Genome Res, Vol., pp.). CGH, however, is not well-suited to identify regions of the genome which have undergone LOH such that a single allele is present but there is no reduction in copy number.

With the completion of the human genome, single nucleotide polymorphisms (SNPs), the most common sequence variation among individuals, are emerging as the marker of choice in large-scale genetic studies due to their abundance, stability, and relative ease of scoring. These same characteristics make SNPs powerful markers for LOH studies.

SUMMARY OF THE INVENTION

The current invention provides methods, systems and computer software products suitable for analyzing data from nucleic acid arrays to detect changes in copy number and to estimate copy number. The probe arrays may be, for example, genotyping arrays that employ multiple probes against each of a plurality of SNPs to determine genotype of individual SNPs or arrays of probes that are spaced at approximately equal distances throughout a genome or a portion of a genome, for example, every 100 bases over an entire chromosome.

In one embodiment a method for identifying regions of genomic amplification and deletion in an experimental sample is disclosed. The sample is prepared by isolating nucleic acid from the experimental sample; amplifying at least some regions of the nucleic acid; labeling the amplified products. The labeled amplified products are hybridized to a genotyping array to obtain a hybridization pattern. The genotyping array comprises a plurality of genotyping probe sets for a plurality of SNPs. A probe set comprises: a plurality of perfect match probes to a first allele of a SNP, a plurality of perfect match probes to a second allele of the SNP, a plurality of mismatch probes to the first allele of the SNP, and a plurality of mismatch probes to the second allele of the SNP. The hybridization pattern is used to obtaining a measurement for the SNP in the experimental sample. The measurement, S, is the log of the arithmetic average of the intensities of the perfect match probes for the SNP in the hybridization pattern. An S value is also calculated for the SNP in each of a plurality of reference samples that are matched to the experimental sample in genotype call. The mean and the standard deviation for the reference samples are calculated using the values obtained in S values and a log intensity difference is calculated by subtracting the mean values for the reference and experimental samples. The copy number of the region including the SNP is estimated by using the difference between the mean for the SNP in the reference samples and the S value for the SNP in the experimental sample in a log-log linear model.

In one embodiment the S values for all SNPs genotyped in the experimental sample and in each reference sample are normalized so that the mean for all the autosomal SNPs in a sample is zero and the variance is 1.

In another embodiment a p-value is calculated for the estimated copy number alteration and if the p-value is less than a threshold p-value the estimated direction of copy number change is significant.

In a preferred embodiment the S value is calculated using:

$$S = \text{Log}\left(\frac{1}{X}\sum_{i=1}^{X} PM_i\right)$$

where $PM_i$ is the intensity of the perfect match cell of probe pair i and X is the number of perfect match probes in a set. The number of perfect match probes used to calculate S may be between 1 and 30. In a preferred embodiment 20 PM probes are used.

In one embodiment the copy number is estimated using:

$$\text{Copy Number} \approx \exp(0.693 + 0.895 \times (\tilde{S}_{jg}^{C} - \hat{\mu}_{jg}))$$

wherein $S_{jg}^{C}$ is the log of the average of the intensities of the perfect match probes for a SNP j of genotype g in an experimental sample c, normalized to the S values of all SNPs genotyped in the experimental sample and $\hat{\mu}_{jg}$ is the average mean of the normalized S values for SNP j in a plurality of reference samples of genotype g at SNP j.

In another embodiment a p-value is calculated for the direction of estimated copy number alteration using:

$$p_j = \min\left(1 - \Phi\left(\frac{\tilde{S}_{jg}^{C} - \hat{\mu}_{jg}}{\hat{\sigma}_{jg}}\right), \Phi\left(\frac{\tilde{S}_{jg}^{C} - \hat{\mu}_{jg}}{\hat{\sigma}_{jg}}\right)\right).$$

The p-value obtained is used to determine if the direction of the estimate is significant.

The experimental sample may be from a tumor, a mixture of tumor and normal cells or non-cancerous cells that may be from a source suspected of having a disease.

In another embodiment copy number is estimated using:

$$\text{Copy Number} \approx \exp(b + m \times (\tilde{S}_{jg}^{C} - \hat{\mu}_{jg}))$$

wherein $S_{jg}^{C}$ is the log of the intensities of the perfect match probes for a SNP j of genotype g in an experimental sample c, normalized to the S values of all SNPs genotyped in the experimental sample, $\hat{\mu}_{jg}$ is the average mean of the normalized S values for SNP j in a plurality of reference samples of genotype g at SNP j, b is the y-intercept and m is the slope of a line defined by plotting intensity values from SNPs of known copy number. In one embodiment the line is defined by plotting intensity values from SNPs on the X chromosome using control samples with varying numbers of X chromosomes.

In another embodiment a second estimate of copy number is obtained by comparing the discrimination ratio, DR, of a SNP in an experimental sample with an average DR from that SNP in a plurality of genotype matched reference samples, where the DR for a probe set with 20 PM/MM probe pairs is calculated using:

$$DR = \frac{1}{20}\sum_{i=1}^{20}\left(\frac{PM_i - MM_i}{PM_i + MM_i}\right)$$

In another embodiment each S value obtained that is more than 3 standard deviations from the mean of the S values is excluded from the estimation of mean and variance of the reference distribution.

In another embodiment at least one region of loss of heterozygosity is identified in an experimental sample by identifying at least one contiguous stretch of homozygous SNP genotype calls in the genome of an experimental sample; obtaining a probability, $\hat{P}_i$ of homozygosity for each SNP in the contiguous stretch wherein $$\hat{P}_i = \frac{\text{\# of } AA \text{ or } BB \text{ calls on } SNP\,i}{\text{total \# of genotype calls on } SNP\,i};$$

calculating the probability that each of the SNPs in the contiguous stretch is homozygous by using:

$$\hat{P}(SNP\ m\ \text{to}\ n\ \text{homozygous}) = \prod_{i=m}^{n} \hat{P}_i;$$

and, identifying the region containing the SNPs as a region of loss of heterozygosity if $\hat{P}(SNP\ m\ \text{to}\ n\ \text{homozygous})$ is less than a p-value threshold. The number of SNPs in the contiguous stretch may be, for example, from 10 to 100.

In another embodiment a method copy number is estimated for a region identified as a region of loss of heterozygosity by calculating an S value for at least one of the SNPs in the identified region in the experimental sample using:

$$S = \text{Log}\left(\frac{1}{X}\sum_{i=1}^{X} PM_i\right)$$

where $PM_i$ is the intensity of the perfect match cell of probe pair i and X is the number of probe pairs in a set and normalizing the S value; normalized S values are calculated for the at least one SNP from a plurality of matched genotpye call reference samples and an average of the reference sample normalized S values is calculated for the SNP. The normalized S value for the SNP in the experimental sample is compared with the average of the normalized S values for the SNP in the reference sample to obtain a ratio; and the copy number of the SNP in the experimental sample is estimated using a log-log linear model. This may be done for 2 or more SNPs in the sample and a p-value may be calculated.

In another embodiment the copy number estimates of two or more consecutive SNPs is evaluated for significance by identifying a stretch of contiguous SNPs that either all show a reduction in copy number or all show an increase in copy number relative to a plurality of reference samples; calculating $\tilde{z}_{m,n}$ using $$\tilde{z}_{m,n} = \frac{1}{\sqrt{n-m+1}}\sum_{j=m}^{n}\hat{z}_{jg} \sim N(0,1);$$

converting $\tilde{z}_{m,n}$ to a probability using the standard $\Phi$ function to obtain a p-value; and, concluding that the estimates are significant using a p-value threshold.

In another embodiment one or more regions of loss of heterozygosity are detected in an experimental sample by amplifying a collection of target sequences from said experimental sample; hybridizing the amplified target sequences to an array of probes designed to interrogate a collection of polymorphisms in the collection of target sequences by allele specific hybridization to generate a hybridization pattern from the experimental sample wherein the hybridization pattern comprises intensity measurements for perfect match and mismatch probes for a plurality of SNPs. An average hybridization intensity for the perfect match probes for each SNP in the experimental sample is calculated and the average hybridization intensities for all SNPs on the array are normalized. A SNP discrimination ratio for each SNP on the array is calculated. Individual SNP discrimination ratios and hybridization intensities from the experminental sample are compared to SNP discrimination ratios and hybridization intensities that are an average of SNP discrimination ratios and hybridization intensities for individual SNPs from a plurality of reference samples wherein variability within the reference sample is considered and regions with changes in DNA copy number in the experimental sample are identified.

BRIEF DESCRIPTION OF THE FIGURES

The accompanying drawings, which are incorporated in and form a part of this specification, illustrate embodiments of the invention and, together with the description, serve to explain the principles of the invention:

FIG. 3A shows individual plots and 3B shows the plot of log intensity ratio versus log copy number, showing a linear relationship observed with the experimental values.

Figure 1:
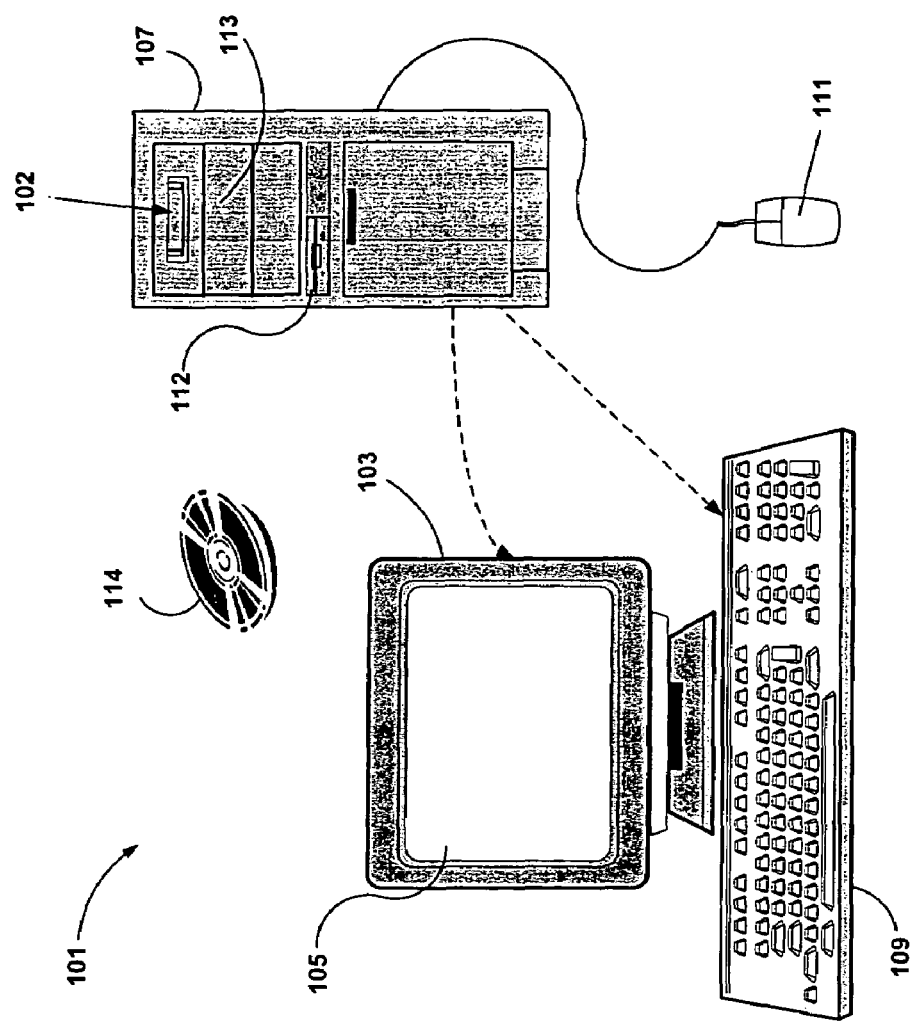
FIG. 1 illustrates an example of a computer system that may be utilized to execute the software of an embodiment of the invention.

DETAILED DESCRIPTION OF THE INVENTION (A) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. All references to the function log default to e as the base (natural log) unless stated otherwise (such as $\log_{10}$).

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GENECHIP® Example arrays are shown on the website at affymetrix.com.

The present invention also contemplates many uses for polymers attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. patent application Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N.Y, 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. patent application Ser. No. 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001).

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. patent application Ser. Nos. 10/063,559, 60/349,546, 60/376,003, 60/394,574, 60/403,381.

The present invention is related to U.S. patent application Ser. No. 10/264,945 and U.S. Provisional Patent application Nos. 60/417,190 and 60/319,685 which are herein incorporated by reference in their entirety for all purposes.

(B) Definitions

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry*, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An oligonucleotide or polynucleotide is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term fragment refers to a portion of a larger DNA polynucleotide or DNA. A polynucleotide, for example, can be broken up, or fragmented into, a plurality of fragments. Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," 3$^{rd}$ Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

Adaptor sequences or adaptors are generally oligonucleotides of at least 5, 10, or 15 bases and preferably no more than 50 or 60 bases in length, however, they may be even longer, up to 100 or 200 bases. Adaptor sequences may be synthesized using any methods known to those of skill in the art. For the purposes of this invention they may, as options, comprise templates for PCR primers, restriction sites and promoters. The adaptor may be entirely or substantially double stranded. The adaptor may be phosphorylated or unphosphorylated on one or both strands. Adaptors are particularly useful in one embodiment of the current invention if they comprise a substantially double stranded region and short single stranded regions which are complementary to the single stranded region created by digestion with a restriction enzyme. For example, when DNA is digested with the restriction enzyme EcoRI the resulting double stranded fragments are flanked at either end by the single stranded overhang 5'-AATT-3', an adaptor that carries a single stranded overhang 5'-AATT-3' will hybridize to the fragment through complementarity between the overhanging regions. This "sticky end" hybridization of the adaptor to the fragment may facilitate ligation of the adaptor to the fragment but blunt ended ligation is also possible.

"Genome" designates or denotes the complete, single-copy set of genetic instructions for an organism as coded into the DNA of the organism. A genome may be multi-chromosomal such that the DNA is cellularly distributed among a plurality of individual chromosomes. For example, in human there are 22 pairs of chromosomes plus a gender associated XX or XY pair.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

The term subset or representative subset refers to a fraction of a genome. The subset may be 0.1, 1, 3, 5, 10, 25, 50 or 75% of the genome. The partitioning of fragments into subsets may be done according to a variety of physical characteristics of individual fragments. For example, fragments may be divided into subsets according to size, according to the particular combination of restriction sites at the ends of the fragment, or based on the presence or absence of one or more particular sequences.

An "array" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., Science, 251:767-777 (1991). Each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789, 162, 5,708,153, 6,040,193 and 5,800,992, which are hereby incorporated by reference in their entirety for all purposes.)

Arrays may be packaged in such a manner as to allow for diagnostic use or can be an all-inclusive device; e.g., U.S. Pat.

Nos. 5,856,174 and 5,922,591 which are incorporated herein by reference in their entirety for all purposes.

Preferred arrays are commercially available from Affymetrix under the brand name GENECHIP® and are directed to a variety of purposes, including genotyping and gene expression monitoring for a variety of eukaryotic and prokaryotic species. (See Affymetrix Inc., Santa Clara and their website at affymetrix.com.)

Hybridization probes are oligonucleotides capable of binding in a base-specific manner to a complementary strand of nucleic acid. Such probes include peptide nucleic acids, as described in Nielsen et al., *Science* 254, 1497-1500 (1991), and other nucleic acid analogs and nucleic acid mimetics. See U.S. patent application Ser. No. 08/630,427-filed Apr. 3, 1996.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

Polymorphism refers to the occurrence of two or more genetically determined alternative sequences or alleles in a population. A polymorphic marker or site is the locus at which divergence occurs. Preferred markers have at least two alleles, each occurring at frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The diallelic form occurring most frequently in a selected population is sometimes referred to as the wildtype form. Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur at equal frequency, and linked locus Y has alleles c and d, which occur at equal frequency, one would expect the combination ac to occur at a frequency of 0.25. If ac occurs more frequently, then alleles a and c are in linkage disequilibrium. Linkage disequilibrium may result, for example, because the regions are physically close, from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

Normal cells that are heterozygous at one or more loci may give rise to tumor cells that are homozygous at those loci. This loss of heterozygosity may result from structural deletion of normal genes or loss of the chromosome carrying the normal gene, mitotic recombination between normal and mutant genes, followed by formation of daughter cells homozygous for deleted or inactivated (mutant) genes; or loss of the chromosome with the normal gene and duplication of the chromosome with the deleted or inactivated (mutant) gene.

A homozygous deletion is a deletion of both copies of a gene or of a genomic region. Diploid organisms generally have two copies of each autosomal chromosome and therefore have two copies of any selected genomic region. If both copies of a genomic region are absent the cell or sample has a homozygous deletion of that region. Similarly, a hemizygous deletion is a deletion of one copy of a gene or of a genomic region.

Genetic rearrangement occurs when errors occur in DNA replication and cross over occurs between nonhomologous regions resulting in genetic material moving from one chromosomal location to another. Rearrangement may result in altered expression of the genes near the rearrangement.

An aneuploid is a cell whose chromosomal constitution has changed from the true diploid, for example, extra copies of a chromosome or chromosomal region.

An individual is not limited to a human being, but may also include other organisms including but not limited to mammals, plants, bacteria or cells derived from any of the above.

The Whole Genome Sampling Assay (WGSA) reduces the complexity of a nucleic acid sample by amplifying a subset of the fragments in the sample. A nucleic acid sample is fragmented with one or more restriction enzymes and an adapter is ligated to both ends of the fragments. A primer that is complementary to the adapter sequence is used to amplify the fragments using PCR. During PCR fragments of a selected size range are selectively amplified. The size range may be, for example, 400-800 or 400 to 2000 base pairs. Fragments that are outside the selected size range are not efficiently amplified.

The fragments that are amplified by WGSA may be predicted by in silico digestion and an array may be designed to genotype SNPs that are predicted to be amplified. Genotyping may be done by allele specific hybridization with probes that are perfectly complementary to individual alleles of a SNP. A set of probes that are complementary to the region surrounding each SNP may be present on the array. Perfect match probes are complementary to the target over the entire length of the probe. Mismatch probes are identical to PM probes except for a single mismatch base. The mismatch position is typically the central position so for a 25 base probe the mismatch is position 13.

The methods may be combined with other methods of genome analysis and complexity reduction. Other methods of complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592, 6,458,530 and U.S. Patent application Nos. 20030039069, 09/916,135, 09/920,491, 09/910,292 and 10/264,945, which are incorporated herein by reference in their entireties.

The design and use of allele-specific probes for analyzing polymorphisms is described by e.g., Saiki et al., *Nature* 324, 163-166 (1986); Dattagupta, EP 235,726, Saiki, and WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles.

(C) Detection of Changes in Copy Number

Genetic instability, such as changes in DNA copy number, is one of the hallmarks of many human cancers. High-density DNA array technology has been applied towards the identification of genomic alterations in tumor cells, most notably LOH (Lindblad-Toh, et al. (2000), *Nat Biotechnol*, Vol. 18, pp.1001-5, Mei, R., et al. (2000), *Genome Res*, Vol. 10, pp.1126-37, Schubert, et al. (2002), *Am J Pathol*, Vol. 160, pp.73-9, and Dumur et al. (2003), *Genomics*, Vol. 81, pp.260-9). Methods are disclosed for using high density arrays for detection of LOH and genomic amplifications and deletions. In many embodiments the high density array is a genotyping array. However, other arrays of probes may be used, for example, an array of probes complementary to different regions of human genes, such as the Human Genome U133 Plus 2.0, available from Affymetrix, Inc, Santa Clara may be used. In general the methods compare the intensity of hybridization of nucleic acids to perfect match probes and correlate higher intensity with higher copy number. The relationship between log intensity and log copy number was found to be approximately linear and using control samples of known copy number the slope and y-intercept of the line may be estimated.

Methods of genotyping many polymorphisms in parallel may be used to identify DNA gains and losses across multiple chromosomes. Methods that reduce complexity of a genomic sample in a predictable way can be used in combination with an array of probes designed to interrogate polymorphisms in the resulting reduced complexity genomic sample. Methods such as those disclosed in U.S. patent application Ser. No. 10/264,945 may be used to detect genotypes and the genotype information may be used to identify regions of homozygous deletion or regions of gene amplification. A single primer may be used to amplify representative fractions of the genome followed by SNP genotyping via hybridization to high density oligonucleotide arrays which comprise perfect match (PM) and mismatch (MM) probe sets from one or both strands of the DNA. Algorithms that use, for example, discrimination ratios between paired PM and MM intensity values may be used to identify regions of homozygous deletions or median PM intensities may be used to identify regions of gene amplification. Following chip intensity normalization, SNP discrimination ratios and PM intensities from an experimental sample may be compared to distributions derived from a references set containing normal individuals. In one embodiment the sample set contains over 100, 400, 500, or 1,000 individuals, allowing statistically significant regions with DNA copy number changes to be identified. Additionally, statistically significant genomic intervals showing loss of heterozygosity (LOH) may be identified by calculating the likelkhood of a contiguous stretch of homozygous markers based on known allele frequencies. The SNPs are SNPs that are genotyped on the array being used and there may be SNPs in between the genotyped SNPs that are not genotyped. The allele frequencies may be obtained, for example, from a publicly available database, such as dbSNP, by genotyping a reference set of samples, or from any available database of allele frequencies. Using a data set derived from a single array, a sample can be analyzed for LOH, deletions, and amplifications. In one embodiment an array that has mean and median inter-SNP distances of about 250 kb and 120 kb respectively may be used. In another embodiment the mean and median inter-SNP distances are less than 100 kb and 20 kb respectively. This method may be used to detect copy number changes in any sample. In a preferred embodiment the tissue is a tissue that is suspected of being a cancerous tissue, for example, human breast cancer, prostate cancer, lung cancer and colon cancer.

Methods are disclosed for identifying chromosomal gains and losses at high resolution using high-density microarray genotyping methods such as whole genome sampling analysis (WGSA) (see, Kennedy et al. (2003), *Nat Biotechnol*, Vol., pp.1233-1237, and U.S. patent application Ser. Nos. 09/920, 492, 09/904,039, 10/681,773, 10/316,517, 10/442,021, 10/463,991, 10/316, 629, and 10/264,945 and U.S. Pat. No. 6,361,947). WGSA simultaneously genotypes more than 10,000 SNPs in parallel by allele-specific hybridization to perfect match (PM) and mismatch (MM) probes synthesized on an array.

In one aspect of the invention, methods are provided for using SNP genotyping to identify DNA copy number changes. SNP genotyping can be performed using a number of suitable methods, including genotyping arrays such as the 10K SNP array (Available from Affymetrix, Santa Clara, Calif.) using the Whole Genome Sampling Assay (WGSA) or other methods of amplification that may or may not involve complexity reduction. Arrays with larger numbers of SNPs may also be used along with any available method of genome amplification. The methods will be described using the Affymetrix 10K SNP array as examples. However, one of skill in the art would appreciate that the methods are not limited to the 10K SNP array. Any array that has perfect match probes that are complementary to regions of the genome may be used. In one embodiment an array is designed to have probe sets comprising perfect match probes for regions that are spread out throughout a genome. For example, the array may have probe sets that are spaced approximately 25 bp, 100 bp, 1 kb, 5 kb, 10 kb or 100 kb apart throughout an entire genome. The array may have probes for a single organism or for two or more organisms. The probe sets may have between 1, 2, 5, 10, 15, 20, 30 or more perfect match probes. Probes may be in probe pairs with a PM and MM probe or the MM probes may be left off the array.

FIG. 1 illustrates an example of a computer system that may be used to execute the software of an embodiment of the invention. FIG. 1 shows a computer system 101 that includes a display 103, screen 105, cabinet 107, keyboard 109, and mouse 111. Mouse 111 may have one or more buttons for interacting with a graphic user interface. Cabinet 107 houses a floppy drive 112, CD-ROM or DVD-ROM drive 102, system memory and a hard drive (113) (see also FIG. 2) which may be utilized to store and retrieve software programs incorporating computer code that implements the invention, data for use with the invention and the like. Although a CD 114 is shown as an exemplary computer readable medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
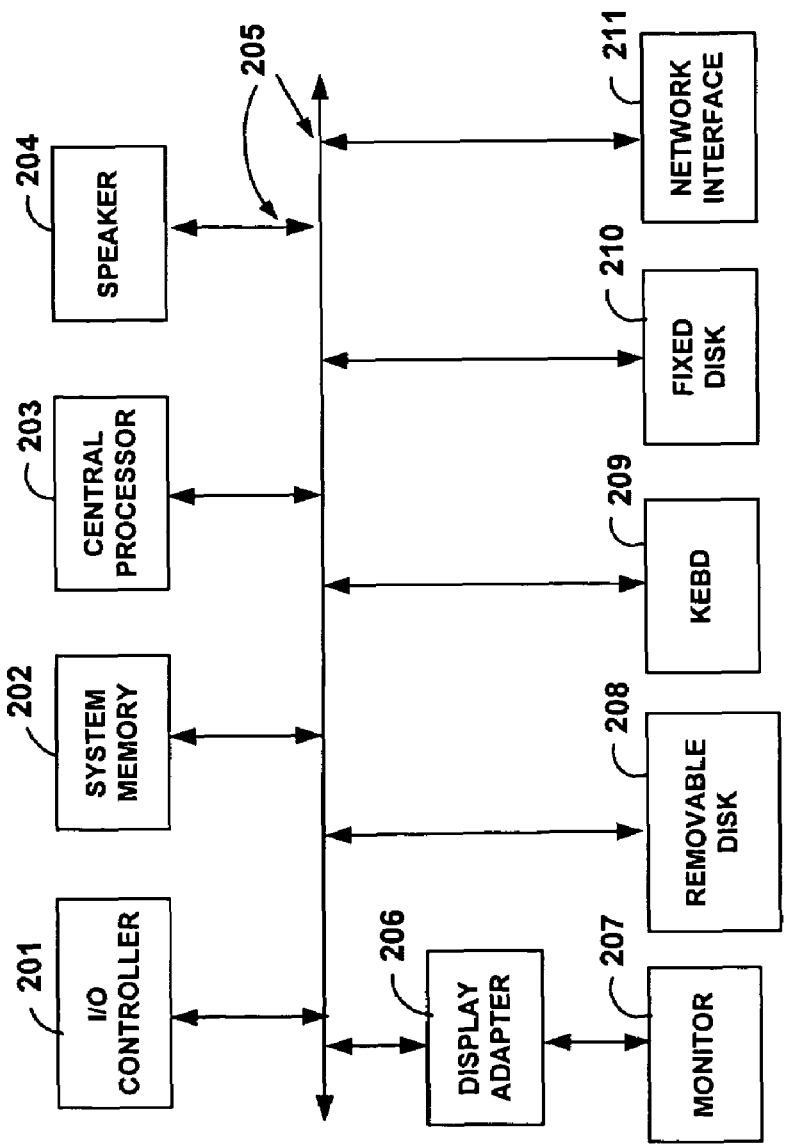
FIG. 2 illustrates a system block diagram of the computer system of FIG. 1.
Figure 3:
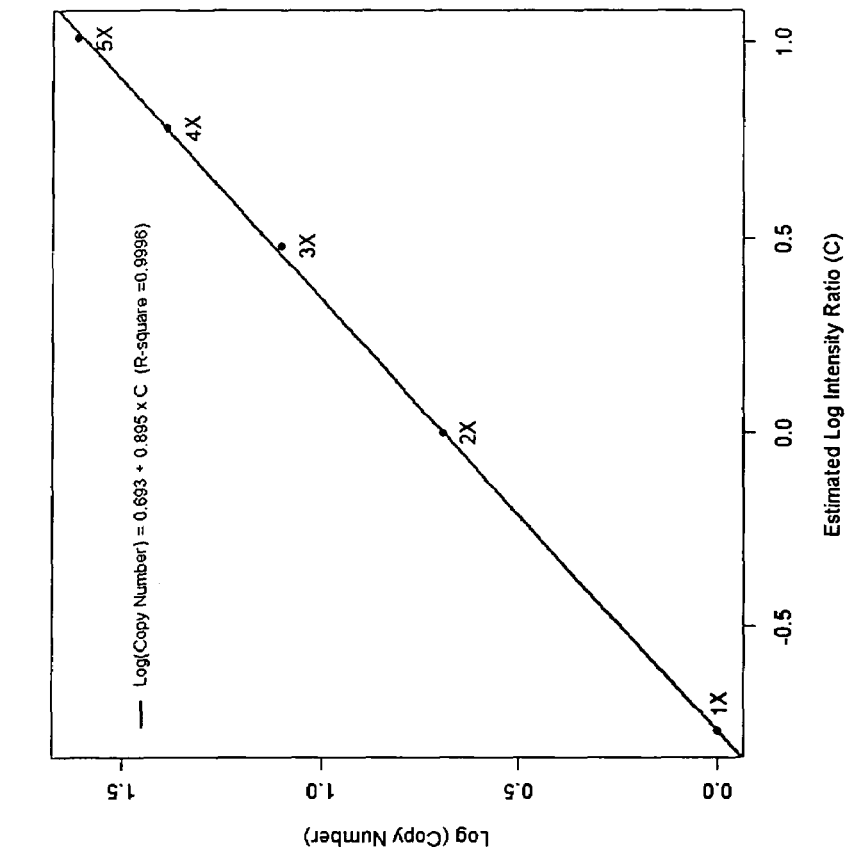
FIG. 3 shows a plot of the log intensity of SNPs on the X chromosome from an individual with 1, 3, 4 or 5 copies of the X chromosome compared to an individual with 2 copies of the X chromosome.
Figure 3:
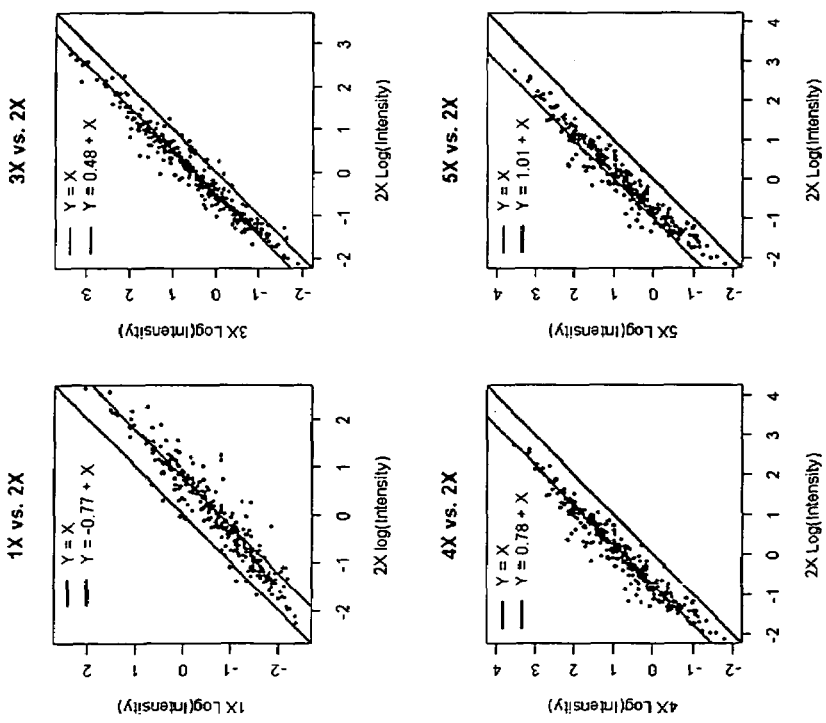

FIG. 2 shows a system block diagram of computer system 101 used to execute the software of an embodiment of the invention. As in FIG. 1, computer system 101 includes monitor 201, and keyboard 209. Computer system 101 further includes subsystems such as a central processor 203 (such as a Pentium™ III processor from Intel), system memory 202, fixed storage 210 (e.g., hard drive), removable storage 208 (e.g., floppy or CD-ROM), display adapter 206, speakers 204, and network interface 211. Other computer systems suitable for use with the invention may include additional or fewer subsystems. For example, another computer system may include more than one processor 203 or a cache memory. Computer systems suitable for use with the invention may also be embedded in a measurement instrument.

In a preferred embodiment copy number is estimated by comparing an intensity measurement for a SNP in an experimental sample to a distribution of intensity measurements from the same SNP in a plurality of reference samples. In one embodiment the reference set may be, for example, more than 10, 100, 200, 300 or 500 normal individuals, allowing statistically significant regions to be identified. In a preferred embodiment the data points selected for the plurality of reference samples used to calculate the normal distribution for a particular SNP are matched in genotype call to the experimental sample, for example, if the experimental sample has a genotype call of AA then reference samples that also have an AA call are selected to generate the normal distribution for this SNP. If the number of reference samples matching the experimental sample in genotype call is too small or if the genotype call for the experimental sample is "No Call" all reference samples may be used irrespective of genotype call.

Generally the steps of the method are to obtain an intensity measurement for a SNP in an experimental sample, obtain intensity measurements for the SNP in a plurality of samples that have a genotype call that is matched to the experimental sample and calculate an average intensity for that SNP in the plurality of normal samples, compare the measurements to obtain a ratio between the intensity measurement for the normal samples and the intensity measurement for the experimental sample, estimate the copy number in the experimental sample using the linear relationship between the log of the intensity and the log of copy number, calculate a p-value for the estimated copy number to determine a confidence level for the estimate and concluding that the confidence level is high if the p-value is lower than a selected threshold. The threshold may be, for example $10^{-4}$ or $10^{-6}$.

The method may be used with pure tumor samples or mixed samples, containing both normal and tumor DNA, but the methods may be used with any sample. In one embodiment the methods may be used to detect copy number changes in samples to determine if the sample is normal or has copy number changes. For example, the methods may be used for pre-natal diagnosis of diseases that correlate with amplification or deletion of genomic regions.

The methods disclose a molecular approach that may be used to identify within a single experiment regions of allelic loss along with regions of amplification that may lead to improved understanding of the cancer genome. The methods may be used to diagnose disease, for example cancer or diseases resulting from allelic imbalance. The methods may also be used to monitor treatment regimens to determine if a particular treatment results in changes in copy number of genomic regions.

In one embodiment known allele frequencies from a reference set are used to identify genomic intervals that contain contiguous stretches of homozygous markers, allowing for the detection of regions of loss of heterozygosity (LOH) without the need for a matched normal control sample. Methods are also disclosed for determining the probability that the genomic intervals can be identified In one embodiment genomic DNA is amplified directly without complexity reduction. One method for amplifying genomic DNA, Multiple Displacement Amplification (MDA), is described in Hosono S, et al. *Genome Res.* 13:954-64 (2003), Dean et al. *Proc Natl Acad Sci USA.* 16;99(8):5261-6 (2002) and U.S. Pat. No. 6,617,137. MDA is an isothermal, strand-displacing amplification yielding about 20-30 um product from as few as 1-10 copies of human genomic DNA. Amplification can be carried out directly from biological samples including crude whole blood and tissue culture cells.

In one embodiment DNA samples with varying X chromosome copies (from 1X to 5X) are used to model the relationship between copy number and hybridization intensity.

Deletion and Amplification Detection

Cross-hybridization can give artificially high intensity values when no target exists and using the intensity measure alone may result in failure to detect some deletions. In one embodiment discrimination ratio (DR) is used to detect deletions either alone or in combination with methods that use ratios of PM intensity averages. In one embodiment the discrimination ratio data is weighted more than the intensity data in deletion detection.

If a SNP is deleted, the discrimination ratios of the experimental samples are expected to be very low on both sense and anti-sense strands compared to the normal reference samples. Thus a very significant p-value should be obtained and the SNP is labeled as deleted. For an amplified SNP the experimental sample will have a higher intensity (measured by PM) compared to the normal samples on both strands and is labeled as amplified. This analysis does not require information from neighboring SNPs to identify putative deletions and amplifications so resolution is at the individual SNP level.

In one embodiment the p-values may be plotted against the chromosomal position to identify interesting regions that are amplified or deleted. Distinct and significant regions of amplification or deletion represented by neighboring SNPs that are assayed by the array may be identified in this way. The higher the resolution of SNPs the better refined the regions of amplification and deletion that may be identified.

Estimation of Copy Number Change

In a preferred embodiment a linear relationship is identified using samples of known copy number. In a preferred embodiment the log of the intensity ratio is linearly related to the log of the copy number change. In another embodiment a linear relationship is identified between copy number and intensity ratio. In a preferred embodiment the copy number is up to about 50, but copy numbers as high as 1000 have been shown to correlate with log intensity using the disclosed methods.

In one embodiment a method for estimating genome wide copy number using a high density oligonucleotide array is disclosed. The analysis of LOH is coupled with DNA gains and losses, novel structures may be identified. A comparison to a reference set consisting of more than one hundred normal individuals allows p-values to be computed, and statistically significant gains and losses can be identified. SNP-specific reference distributions are used to account for the inherent variance in normalized signal intensities across probe sets.

In one embodiment individual SNP analysis is used as an initial approach. In another embodiment meta-analysis is used. In meta analysis consecutive SNPs displaying a consistent trend towards gains or losses are given additional weight and significance. Meta-analysis may improve the sensitivity in the example of the X chromosome copy number alterations as well as the signal to noise ratio in the case of autosomal SNPs. However meta-analysis may require caution due to a bias towards long regions of copy number change and may underestimate complex structures which do not span large distances. Also, regions near the boundary of copy number changes in which moderate yet consistent signals are detected may lead to an overestimation of the absolute length of the alteration with meta-analysis. Thus the absolute false positive rate for a given p-value threshold using individual analysis is lower than meta-analysis for both the X chromosome and autosomes. Both approaches use the normal reference set, and thus an inevitable issue with greater than 10,000 markers is the multiple hypothesis testing problem. As a partial solution, the p-value threshold may be stringently set so as to ensure high specificity (low false positive rate) with concomitant lower sensitivity (higher false negative rate) with regard to gains and losses.

In one embodiment meta-analysis may be a preferred embodiment for a screening tool when the identification of all putative moderate alterations (high true positive rate) is needed while individual analysis may be the preferred embodiment for a diagnostic tool due to high specificity. Since gene amplifications can be relatively simple continuous regions ranging from one to several hundred Kb, such as in neuroblastomas (Amler, L. C., and Schwab, M., (1989), *Mol Cell Biol*, Vol. 9, pp.4903-13), or can be complex, irregular regions up to 20 Mb as seen in breast cancers (Guan et al. (1994), *Nat Genet*, Vol. 8, pp.155-61 and Szepetowski et al. (1993), *Genomics*, Vol. 16, pp.745-50), single point analysis may be essential. There are several alternative statistical methods that may be used to analyze the array data such as kernel smoothing to average neighboring points, change point methods and Hidden Markov Chain models. In one embodiment these approaches are developed using true positive control samples which contain a range of defined alterations with respect to length and copy number to train the models.

In one embodiment regions that may have undergone LOH are identified using a probability-based model in lieu of conventional methods using paired samples, allowing analysis of unmatched cancer samples. This approach calculates the likelihood of a stretch of homozygous genotype calls by using allele frequencies derived from the normal reference set. This model-based approach can therefore serve as a guideline to regions of LOH in cases where a normal control sample is not available. Since regions of linkage disequilibrium can vary across the genome, the probability model may tend to overestimate the significance of regions of LOH by treating each SNP independently. Once a significant stretch of homozygosity is identified, the interpretation of whether it truly represents LOH may be difficult due to the presence of homozygous segments in the human genome (Clark, J. et al. (2002), *Genes Chromosomes Cancer*, Vol. 34, pp.104-14). Using 8,000 short tandem-repeat polymorphisms, several CEPH families showed homozygous segments greater than 10 cM (Broman, K. W., and Weber, J. L., (1999), *Am J Hum Genet*, Vol. 65, pp.1493-500).

In one embodiment LOH is identified in a mixture of tumor and normal cells. The mixture may contain, for example, up to 30% normal DNA and 70% or more tumor DNA and greater than 75% of the SNPs undergoing LOH may be identified. In one embodiment the normal DNA is up to 50% of the DNA and the tumor DNA is 50% or more of the DNA.

In some embodiments DNA is amplified by multiplex locus-specific PCR. In a preferred embodiment the DNA is amplified using adaptor-ligation and single primer PCR. Other available methods of amplification, such as balanced PCR (Makrigiorgos, et al. (2002), *Nat Biotechnol*, Vol. 20, pp.936-9), may also be used.

In another embodiment transcriptional profiles of samples are combined with copy number profiles to identify functional roles for genomic regions with allelic imbalances.

In another embodiment the methods are scaled to accommodate SNP information from more than 100,000, 200,000, 500,000 or 1,000,000 SNPs, allowing high resolution analysis across the genome to elucidate genomic changes underlying the complex chromosomal make-up of tumor cells.

Feature Extraction: The Mapping 10K Array has 20 probe pairs (25 mers) equally divided between the sense and anti-sense strands for each SNP, with 10 probe pairs for allele A and 10 probe pairs for allele B. A probe pair includes a perfect match cell and a single-base mismatch cell. The log of the arithmetic average of the PM intensities across 20 probes (S)

is used as the basic measurement for any given SNP. It has an approximate Gaussian distribution on each sample $$S = \text{Log}\left(\frac{1}{20}\sum_{i=1}^{20} PM_i\right)$$

where $PM_i$ is the intensity of the perfect match cell of probe pair i. After S is calculated, it is scaled to have a mean of zero and a variance of one for all autosomal SNPs to increase the comparability across samples.

$$\tilde{S}_j = \frac{S_j - \hat{\mu}}{\hat{\sigma}} \text{ where } \hat{\mu} = \frac{1}{J}\sum_j S_j \text{ and } \hat{\sigma} = \sqrt{\frac{1}{J-1}\sum_{j=1}^{j}(S_j - \hat{\mu})^2}$$

j=1, ..., J are all the autosomal SNPs on the chip.

Intensity may be high for homozygous deletions due to non-specific cross-hybridization. In addition to log average intensity (S), discrimination ratio (DR), which measures the difference between perfect match and mismatch probes, is used as a supplementary metric (Liu et al. 2003).

$$DR = \frac{1}{20}\sum_{i=1}^{20}\left(\frac{PM_i - MM_i}{PM_i + MM_i}\right)$$

In a preferred embodiment the significance of the copy number variation in the target cancer cell line is estimated by a comparison to a normal reference set. The genotype of the target cell line is preferably considered prior to such comparisons such that for each SNP, the cancer cell line is compared to only those normal samples that share the same genotypes. This allows comparisons to be made within a homogeneous distribution instead of a mixture of several subtypes. If the genotype of the target cell line is missing, or the number of reference samples with that particular genotype is small, for example, less than 10, all reference samples may be used to estimate the distribution. The basic assumption is that for any given SNP j and its genotype g (g=AA, AB, or BB) $S_{jg}$ follows a Gaussian distribution (Based on Shapiro-Wilk's W test for normality (see, Royston, P., (1982), Vol. 31, pp.115-124), in one example only 3.3% of the SNPs have p-values less than 0.001 on their reference distribution, which is further reduced to 0.7% when a more stringent cut-off of 0.0001 is used); and the mean and variance of such distributions are estimated using the normal reference samples.

$$\tilde{S}_{jg} \sim N(\mu_{jg}, \sigma_{jg}^2) \quad \hat{\mu}_{jg} = \frac{1}{K_g}\sum_{k=1}^{K_g} \tilde{S}_{jk} \quad \hat{\sigma}_{jg}^2 = \frac{1}{K_g - 1}\sum_{k=1}^{K_g}(\tilde{S}_{jk} - \tilde{\mu}_{jg})^2$$

where k=1, ..., $K_g$ represents the normal samples that have the same genotype g as the target cell line. While the normal samples may contain isolated regions of gains and losses, in a preferred embodiment outlier data points, defined as having values more than three standard deviations away from the mean, are excluded from the estimation of mean and variance of the reference distribution. In one example distribution from 110 references samples more than 90% of the SNP distributions had no outliers, about 9% had one outlier, less than 0.5% had two outliers and less than 0.01% had more than 3 outliers so the total number of outlier points that will be removed is expected to be low.

Assuming the experimental sample has genotype g and value $S_{jg}^C$ on SNP j, the significance of the difference of $S_{jg}^C$ from the normal reference distribution is measured by the p-value:

$$p_j = \min\left(1 - \Phi\left(\frac{\tilde{S}_{jg}^C - \tilde{\mu}_{jg}}{\hat{\sigma}_{jg}}\right), \Phi\left(\frac{\tilde{S}_{jg}^C - \tilde{\mu}_{jg}}{\hat{\sigma}_{jg}}\right)\right)$$

Meta-Analysis

For each SNP j, with genotype g the individual test statistic for the significance calculation is:

$$\hat{z}_{jg} = \frac{\tilde{S}_{jg}^C - \tilde{\mu}_{jg}}{\hat{\sigma}_{jg}}$$

where $\hat{\mu}_{jg}$ is the reference sample mean and $\hat{\sigma}_{jg}$ is the reference sample standard deviation. As previously described, $\hat{z}_{jg}$ is assumed to have a standard normal distribution and SNPs are assumed to be independent. Thus for any given stretch in the genome starting at point m and ending at point n $$\tilde{z}_{m,n} = \frac{1}{\sqrt{n - m + 1}}\sum_{j=m}^{n}\hat{z}_{jg} \sim N(0, 1)$$

This score $\tilde{z}_{m,n}$ can be converted to a probability by using the standard $\Phi$ function, which is called meta p-value and is substituted for the individual p-values of each SNP when appropriate. Meta-analysis is most suitable when consecutive markers show the same direction of alterations. Accordingly, a candidate stretch is defined starting at point m and ending at point n as:

$$\text{sign}(\hat{z}_{mg}) = \text{sign}(\hat{z}_{(m+1)g}) = \ldots = \text{sign}(\hat{z}_{ng})$$

The starting point is from j=1, i.e. the beginning of the chromosome, and a search is performed for such candidate stretches until the end of the chromosome. If the individual p-value is less significant than the meta p-value for any given SNP, the former is substituted by the later.

Loss of Heterozygosity (LOH)

In one embodiment loss of heterozygosity may be estimated by comparison of observed stretches of homozygosity where two or more contiguous SNPs are homozygous and the product of the probability that each of the SNPs will be homozygous determined by observed allele frequencies. Using genotype information, statistically significant genomic intervals showing LOH can be identified by calculating the likelihood of a contiguous stretch of homozygous markers based on known allele frequencies using the same reference set of normal individuals. The probability of being homozygous may be calculated for each individual SNP i:

$$\hat{P}_i = \frac{\# \text{ of } AA \text{ or } BB \text{ calls on } SNPi}{\text{total } \# \text{ of genotype calls on } SNPi}.$$

If each SNP is treated independently, then the probability of a stretch of contiguous SNPs (from position m to position n) all being homozygous will be:

$$\hat{P}(SNP\ m\ \text{to}\ n\ \text{homozygous}) = \prod_{i=m}^{n} \hat{P}_i.$$

After such homozygous stretches are defined, their intensity information may be analyzed, i.e. the p-value and fold-change estimation to determine the copy number change (loss or amplification) of the LOH region. For complete deletion, which is an extreme case of LOH, low discrimination ratio with significant p-value may be used as a confirming measurement.

In another embodiment an array may be designed to detect the presence or absence of fragments that are predicted to be present in an amplified sample resulting from complexity reduction amplification of a genomic sample, such as WGSA. A 25 mer probe may be designed for each region that is predicted to be present in the amplified sample. The reduced complexity sample is generated and hybridized to the array and the hybridization pattern is analyzed to identify regions that are missing. In one embodiment a probe is designed for every 100 basepair region predicted to be present in a reduced complexity sample. An experimental sample is amplified and hybridized to the array and regions where hybridization is absent or reduced are indicative of loss of that region from the genomic sample.

In one embodiment the genomic sample is human genomic DNA and the sample is digested with XbaI, fragments are ligated to a common adaptor and amplified by PCR. The complexity of the resulting amplified reduced complexity sample is predicted to be about 40 megabases. One 25 mer probe may be designed for every 100 basepairs in the reduced complexity sample resulting in approximately 400,000 perfect match probes and another 400,000 mismatch control probes. Probe lengths may be varied, for example, probes may be 15, 17, 21, 25, or 30-60 nt in length.

Rearrangements in the genome may also be detected. In one embodiment the probes are designed to detect the presence or absence of specific fragments in an amplified reduced complexity sample. In this embodiment, an array designed to detect fragments that are near selected restriction sites and of a selected size range may be used. Genetic rearrangement may result in changes in the size of fragments so that selected fragments are no longer amplified efficiently under the selected conditions. Probes to these fragments will have reduced signal intensity after hybridization and this may indicate rearrangement.

The disclosed methods may be used for a variety of applications. The methods may be used, for example, to track cell division. During cell division DNA is replicated so at any one time some chromosomal regions will be present in extra copies. The method may be used to determine which regions of the genome have been replicated at a selected stage of cell division. The methods may be used to track cross-over hybridization and genetic rearrangements that are often associated with cancer or other disease states. The methods may be used to predict patient outcome or prognosis, to select a treatment regime for a patient or to classify a sample as being cancerous if amplification is detected by the disclosed methods. Different types of cancer may be characterized by amplification of different regions of the genome and amplification of regions to different degrees. The methods may be used to establish criteria for such classifications and for classification of samples according to established criteria.

In a preferred embodiment the methods are used to diagnose cancers. Cancer is often associated with loss of one or more genomic regions, amplification of one or more genomic regions or rearrangement of one or more genomic regions in a tissue sample. Detection of these genomic changes may be used to diagnose cancer or to monitor the stage of a tumor. In one embodiment the amount of gene amplification may be determined in order to identify if the tissue is pre-cancerous or cancerous.

In one embodiment probes are selected according to a probe hybridization model so that the set of probes is optimal for discrimination of the absence or presence of fragments that are predicted to be present in the amplified reduced complexity sample. Using in silico digestion it is possible to predict the fragments that will result when a genome is digested with a given enzyme or combination of enzymes and the probes may be designed to detect the presence or absence of fragments predicted to be present using in silico digestion. In some embodiments a computer system is used to predict which sequences will be present in a reduced complexity sample where the complexity is reduced by a selected method.

Any method of complexity reduction that results in the amplification of a predictable subset of fragments may be used to produce a reduced complexity sample. The array may be designed depending on the complexity reduction method being used and the fragments predicted to be present in the reduced complexity sample. Other methods of complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. patent application Ser. Nos. 09/512,300, 09/916,135, 09/920, 491, 09/910,292, 10/013,598, and 10/264,945 which are incorporated herein by reference in their entireties.

Amplification methods may be optimized to amplify a subset of these fragments, for example, the fragments that are 400 to 800 basepairs. An array may be designed to detect the presence or absence of the fragments that are predicted to be amplified under a selected set of fragmentation and amplification conditions. The probes on the array may be designed to hybridize to selected regions within each fragment. One or more probes may be designed for each fragment. The probes may be optimized for hybridization using empirical criteria (see, for example, U.S. patent application Ser. No. 10/017, 034 which is incorporated herein by reference in its entirety). Different arrays may be designed depending on the method used to generate the reduced complexity sample.

Prior to hybridization the fragments in the reduced complexity sample may be labeled. In another embodiment the fragments are further amplified prior to hybridization. In some embodiments the fragments are DNA and RNA is synthesized from the fragments and hybridized to an array.

In another embodiment a reduced complexity sample is hybridized to an array that is designed to interrogate all regions of a genome. Probes may be positioned uniformly throughout the genome for example 1 probe approximately every 100, 200, 1000, 2500, 10,000, or 100,000 bases.

In one embodiment the sample is hybridized directly to an array without reducing the complexity of the sample prior to hybridization. The array may be designed to detect the presence of absence of all regions of the genome using representative probes for each region of the genome or to detect selected regions of the genome.

A single primer may be used to amplify representative fractions of the genome followed by SNP genotyping via hybridization to high density oligonucleotide arrays which comprise perfect match (PM) and mismatch (MM) probe sets from one or both strands of the DNA. Algorithms that use, for example, discrimination ratios between paired PM and MM intensity values may be used to identify regions of homozygous deletions or median PM intensities may be used to identify regions of gene amplification. Following chip intensity normalization, SNP discrimination ratios and PM intensities from an experimental sample may be compared to distributions derived from a references set containing normal individuals. In one embodiment the sample set contains over 400, over 500, or over 1,000 individuals, allowing statistically significant regions with DNA copy number changes to be identified. This method may be used to detect copy number changes in any cancerous tissue, for example, breast, prostate, lung, liver, brain, bone, skin, stomach and colon cancers.

Homozygous deletions of certain genes, for example, tumor suppressors, are known to be tumorigenic. Homozygous deletion of p53 is known to be associated with a variety of tumor types. Amplification of certain genes, for example, oncogenes, may result in overexpression of the genes which may be tumorigenic. Examples of oncogenes that are amplified in various tumors include c-myc, c-abl, c-myb, c-erbB, c-K-ras, and mdm2, see Genes VI, B. Lewin (1997) at 1144, which is incorporated herein by reference in its entirety. The method may be used to identify new homozygous deletions that are associated with cancer or another disease or phenotype. In another embodiment the method may be used to determine if an experimental sample has one or more homozygous deletions known or thought to be associated with cancer or another disease or phenotype.

Homozygous deletion of chromosomal regions are also known to cause other disorders, for example, male hypogonadism (Gromoll et al. *J Clin Endocrinol Metab* 85: 2281-2286, 2000), late onset muscular dystropyn (Pulkkinen L, et al., *Hum Mol Genet* 1996:5(10):1539-1546). Homozygous deletions have also been shown to have beneficial phenotypes such as protection against parenteral HIV-1 infection, see Kupfer et al. *AIDS*, June 18;13(9):1025-8, 1999.

The method is not limited to regions of the genome that are known to be expressed or regions that contain known or suspected genes. Probes may be designed to any genomic region. In some embodiments the arrays are designed to exclude probes for regions of know repetitive sequence.

In one embodiment expressed RNA is hybridized to the array and the hybridization pattern from the RNA is compared to a hybridization pattern from a genomic sample. Altered expression of some genetic regions may result in a phenotype that is similar to a homozygous deletion. These genes would appear normal when the genomic material is hybridized to the array but the expression pattern would be altered from normal.

The gene-dosage techniques disclosed may be applied to measure gene copy number for a variety of diseases and applications. In addition to cancer, large genomic duplications and deletions have been found in association with diseases such as alpha-thalassaemia and Duchenne and Becker muscular dystrophies, see, for example, Armour et al. *Human Mutat* 20:325-337 (2002). The method may be used to identify a variety of chromosomal anomalies including, for example: constitutional, acquired, numerical, structural, and mosaicism. A constitutional anomaly affects the individual throughout. The chromosome error was present in the embryo. It may occur before fertilization or in the fertilized zygote. Such disorders include, chromosome inborn syndromes, such as trisomy 21, Turner syndromes, and others. Acquired anomalies affect only one organ with the other tissues being normal, such as cancer. The terms "constitutional" and "acquired" are really quite general terms, and can be applied to any persistent change encountered in clinical practice. A chromosome anomaly may also be homogenous, having all the cells studied carrying the anomaly. Normal cells may be present but not assayed. When only some cells carry the anomaly and others are normal (or carry another anomaly) the sample or individual is a mosaic. Individuals may also have numerical anomalies where one or more chromosomes are present in numbers that are different from normal. Structural changes may occur within a chromosome. The change may be balanced, if there is no loss or gain of genetic material, or unbalanced, if there is deletion and/or duplication of chromosome segment(s).

Additional methods that may be used to relate PM intensity to copy number include algorithms that use stochastic models that take into account neighboring SNPs and incorporate physical data about SNPs into the model. In addition, such methods as hidden Markov chains and Markov chains may be used. For methods of using Hidden Markov Chains see, Rabiner, L. R. and Juang, B. H. (1986) *IEEE ASSP Mag*. 3(1) 4-16 and Rabiner, L. R. (1989) *Proceedings of the IEEE*. 77 257-285. In another embodiment one or a few PM probes are used for detection of amplification or deletion. In one embodiment there are 40 probes that hybridize to the region of a SNP and are used for genotyping the SNP. The probes that work well at discrimination between specific and non-specific hybridization are used for gene dosage analysis using a genotyping array. The probes to be used may be selected by empirical performance of the individual probes. Probe behavior may be analyzed empirically to identify probes that give the most discrimination and highest signal. For Probe Specific Models see Li, C. and Wong, 5 W. H. (2001) *Genome Biology*. 2(8): research0032.1-0032.11, Li, C. and Wong, W. H. (1998) *Proc Natl Acad Sci USA*. 98: 31-36 and Mei, R. et al. (2003) *Proc Natl Acad Sci USA*. 100: 11237-11242. In another embodiment change point analysis is used. For methods of using Change point analysis see Olshen, A. B. and Venkatraman, E. S. (2002). *Proceedings of the Joint Statistical Meetings*, Sen, A. and Srivastava, M. S. (1975). *Ann Statist*. 3 98-108 and Yao, Y-C. (1988) *Statistics & Probability Letters*. 6 181-189. In another embodiment information about linkage disequilibrium (LD) is taken into consideration when identifying regions of LOH. The probability that two neighboring SNPs will be homozygous may be higher than the product of the individual probabilities because of LD between the SNPs because the events are not independent. For LD and LOH estimation, see Balding, D. J., et al. Handbook of statistical genetics. (2001) John Wiley & Sons, LTD.

EXAMPLES

Cell lines and Nucleic Acid Isolation

Nine human breast cancer cell lines (BT-20, MCF-7, MCF-12A, MDA-MB-157, MDA-MB-436, MDA-MB-468, SK-BR-3, ZR-75-1, and ZR-75-30) and two syngeneic human breast cancer cell lines (Hs-578T and Hs-578Bst) (Hackett et al. (1977) *J Natl Cancer Inst*, Vol. 58, pp.1795-806) were obtained from American Type Culture Collection (ATCC). A normal human mammary epithelial cell line (HMEC) was obtained from Clonetics. All cells were grown under recommended culture conditions. Genomic DNA was isolated using QIAGEN QIAAMP™ DNA Blood Mini Kit. DNAs from cell lines containing 3X (NA04626), 4X (NA01416), and 5X (NA06061) chromosomes and DNAs for the normal reference set of 110 individuals (48 males and 62 females)

were purchased from NIGMS Human Genetic Cell Repository, Coriell Institute for Medical Research (Camden, N.J.).

The WGSA assay was performed as described in Kennedy et al. (2003) except for modifications to the target amplification and DNA labeling steps. DNA amplification by PCR was done under following conditions: each 100 μl reaction contained 25 ng of adaptor-ligated genomic DNA, 0.75 μM primer, 250 μM dNTPs, 2.5 mM $MgCl_2$, 10 U AMPLITAQ GOLD™ polymerase (Applied Biosystems (ABI)) in 1X PCR Buffer II (ABI). Cycling was performed as follows: 95° C./3 min, followed with 35 cycles of 95° C./30 sec, 59° C./30 sec, 72° C./30 sec, and an extension at 72° C. for 7 min. The PCR products were purified and concentrated with QIAGEN MinElute PCR Purification kit and DNA concentrations were measured by A 260 nm. Fragmented DNA was labeled in 1 1X TdT buffer with 105 U TdT (Promega) and 0.1429 mM DLR (Affymetrix) at 37° C. for 2 hrs, followed by heat inactivation at 95° C. for 15 min. DNA hybridization to the AFFYMETRIX GENECHIP® 10K Mapping Xba_131 Array, washing, staining, and scanning were performed as specified in the manufacturer's instructions (Affymetrix). All samples except the normal reference set were tested in duplicate. The call rates were all above 88%, The reproducibility was high across all the replicate data. The average genotype concordance was 99.97%, and two key measurements, log intensity (S) and discrimination ratio, both had average correlations between replicates of greater than 0.97.

WGSA DNA mixing experiments were performed as follows: the concentrations of genomic DNA from Hs-578T and Hs-578Bst were determined by PICOGREEN™ dsDNA Quantitation Assay (Molecular Probes) and Hs-578Bst DNA was added to Hs-578T DNA at 10% increments.

Quantitative PCR was performed using ABI Prism 7700 Sequence Detection System (ABI). PCR primers were designed by using Primer Express 1.5 software (ABI) and were synthesized by QIAGEN. Reactions (25 μl containing 25 ng DNA) were prepared using the SYBR-Green PCR Core Reagents kit (ABI). Conditions for amplification were as follows: 1 cycle of 50° C./2 min, 1 cycle of 95° C./10 min, followed by 35 cycles of 95° C./20 sec, 56° C./30 sec, and 72° C./30 sec. Threshold cycle numbers were obtained by using Sequence Detector v1.7a software. Human genomic DNA (Roche) was used as the normal control. All reactions were done in duplicate and threshold cycle numbers were averaged. DNA amounts were measured by UV spectrophotometer and were normalized to LINE-1 elements (9). Relative quantitation was carried out using the comparative Ct method (ABI User Bulletin #2, 1997). Quantitative PCR assays for c-MYC and p16 genes were done as described except that the annealing temperature was 60° C.

Copy Number Estimation and Significance Calculation

In the following example there are three major components to the copy number and significance estimations: (1) dosage response experiments, (2) independent verification of algorithm results using PCR, and (3) confirmation of known true positive regions using the cancer cell line panel. The dosage response between copy number and chip intensity may be tested using samples with varying X chromosome copy numbers, for example 1X to 5X. Using (I) to indicate chip intensity, the dosage response assumption is $I_a \cong C_{ab} \times I_b$, where $I_a$ is the intensity for a region with copy number a, $I_b$ is the intensity on the same region with copy number b, and $C_{ab}$ is the intensity ratio determined by a and b. S is as an approximation of log intensity. Thus a log transformation leads to $S_a \cong S_b + \mathcal{C}_{ab}$, where $\mathcal{C}_{ab}$ is the log intensity ratio determined by a and b.

The log copy number may be estimated by assuming a linear relationship between log copy number and log intensity ratio. A line has the equation y=mx+b where m is the slope of the line and b is the y-intercept. In a preferred embodiment y is the log copy number and C is the log of the intensity ratio. The slope and the y-intercept may be estimated using control sample of known copy number. In one embodiment the slope and y-intercept were determined using samples with known copy numbers of X chromosomes.

Results from DNA samples with 1, 3, 4, and 5X chromosomes were compared to a 2X sample. A high linear correlation was observed among the sample pairs, and for any given pair, the linear trend was parallel to Y=X, confirming the equation $S_a \cong S_b + \mathcal{C}_{ab}$. Using 2X as the baseline, the estimated log intensity ratio ($\mathcal{C}_{ab}$) for each sample showed a strong linear relationship with the log of the copy number. The copy number can be estimated for any given region using the intensity difference. In a preferred embodiment X chromosome results were used to generalize to all autosomes. For SNP j with genotype g and log intensity $S_{jg}{}^C$:

$$\text{Copy Number} \approx \exp(0.693 + 0.895 \times (\tilde{S}_{jg}{}^C - \hat{\mu}_{jg}))$$

A log-log linear model was used because of the general suitability for both low range and high range copy number estimation. $(S_{jg}{}^C - \hat{\mu}_{jg})$ is the log intensity ratio (log x/y=log x−log y). In the high copy number range, the increase in signal intensity will reach a plateau in the assay due to saturation of the probes and a log-log linear relationship may be more appropriate (Bignell et al. (2003), *Submitted*, Vol., pp). These results show that intensity ratios can be used to represent copy number changes and that a log-log linear model is most appropriate to accommodate a wide-range of copy-numbers.

An independent quantitative PCR (qPCR) method to measure DNA copy number changes was used to verify observed regions of chromosomal gains and losses. PCR reactions on a set of 99 autosomal SNPs were carried out using genomic DNA templates from SKBR3 and normal individuals. This set of SNPs was not completely random, and contained both previously known as well as putative novel gains and losses identified in the cancer cell line. An initial qPCR validation experiment was carried out using primer pairs to 7 independent X-chromosome SNPs and ΔCt values for the 1X and 5X DNA samples were determined. While each primer pair showed slight differences in the absolute value of ΔCt following normalization, there was an average difference of 2.23 cycles between the 1X and 5X samples (data not shown). Assuming an amplification efficiency of 2.0, this Ct difference is close to the theoretical value of 2.32. The estimated copy number using WGSA was approximately an exponential function of ΔCt and fell near the theoretical estimating function $2^{\Delta Ct+1}$. The trend is tight when ΔCt values are low and becomes more scattered with increasing ΔCt. A strong positive correlation between ΔCt and the significance level calculated was observed using the algorithm. Except for a few points, the majority of the SNPs with a large ΔCt difference show very strong significance, while SNPs with a small ΔCt difference show moderate to low statistical significance. The results also illustrate the value of discrimination ratio as a supplementary metric to PM intensity. For one data point, the ΔCt value was less than −5, suggesting a homozygous deletion. However, due to possible cross-hybridization, the significance based on PM intensity is only moderate. This SNP shows strong significance with a p-value less than $10^{-6}$ when DR is applied, allowing the deletion to be correctly identified. The relationship between the estimated copy number and the statistical significance was also analyzed. As expected, when the copy number approaches 0 indicating a homozygous deletion, or approaches a large positive number indicating high level amplification, the significance becomes very strong. These combined results indicate that the method can detect chromosomal copy number changes in a quantitative manner.

The breast cancer cell line panel was surveyed for copy number changes in two well characterized regions, namely chromosome 8q and chromosome 9p. CGH analysis of 38 breast cancer cell lines showed gains of 8q in 75% of the samples (Forozan, et al. (2000) *Cancer Res*, Vol. 60, pp.4519-25) and loss of chromosome 9p has been reported in breast cancer (Struski, et al. (2002), *Cancer Genet Cytogenet*, Vol. 135, pp.63-90). Specifically, the c-MYC oncogene at chromosome 8q24 has been shown to be commonly amplified in breast cancer (Escot, et al. (1986), *Proc Natl Acad Sci USA*, Vol. 83, pp.4834-8 and Rummukainen, et al. (2001) *Cancer Genet Cytogenet*, Vol. 126, pp.1-7) while the p16 tumor suppressor on chromosome 9p21 has been shown to be deleted in a variety of tumor types (Kamb, et al. (1994), *Science*, Vol. 264, pp.436-40 and Cairns, et al., (1995), *Nat Genet*, Vol. 11, pp.210-2). Copy number estimates for individual SNPs can be mapped over a region, for example over a chromosome. A genotyping array may provide information about a subset of SNPs that are spread throughout a genome. By looking at the copy number estimate for SNPs that are nearest neighbors in the set of SNPs genotyped by the array, estimates of copy number for larger regions may be made. In one example estimates were compared across four samples for a region of chromosome 8 from 50 to 140 Mb. The genomic region near c-MYC appeared amplified in three cancer cell lines with moderate to very strong significance and did not appear amplified in the normal control (Hs-578Bst). This is consistent with published CGH results that show all three cell lines contain gains in 8q23-q24 (Kallioniemi, et al. (1994), *Proc Natl Acad Sci USA*, Vol. 91, pp.2156-60). Quantitative PCR was carried out with a c-MYC primer pair and confirmed the copy number increase. The estimated c-MYC copy number by qPCR for SK-BR-3, MCF-7, ZR-75-30, and Hs-578Bst is 21, 7.5, 10.6, and 3 respectively. The array used in the example does not contain SNPs from the c-MYC gene itself, but the two nearest SNPs are SNP 55150, which is located 300 Kb proximal to c-MYC, and SNP 511315, which is located 196 Kb distal to c-MYC. WGSA and qPCR results for these SNPs are summarized in Table 1 and confirm that the region surrounding c-MYC is amplified in three of the four cell lines.

The four cell lines were also compared across a region of chromosome 9 from 0 to 40 Mb. WGSA results show three of these cell lines have a significant deletion in the region of p16 as determined by SNP 139369, which is located within the p16 structural gene. This SNP, as well as two flanking SNPs were further analyzed by quantitative PCR and the results are summarized in Table 1. The PCR results independently confirm the p16 deletion. In summary, PCR and the copy number algorithm show highly correlated results for two genomic regions with known alterations, namely c-MYC and p-16.

The SK-BR-3 chromosome 8 analysis and the BT-20 chromosome 9 analysis also illustrate the high resolution capabilities of the disclosed methods. SK-BR-3 shows two adjacent amplified segments near c-MYC. The first, and longer segment, spans from 118.96 to 125.42 Mb. The second shorter segment spans from 127.52 to 127.65 Mb. 12 representative SNPs from the first and second segments were analyzed by PCR and the copy number increase was confirmed. There is a single SNP (719292) disrupting these two segments that is scored as unamplified using both quantitative PCR ($\Delta Ct=-0.3$) and the copy number algorithm (p-value=0.43). BT-20 contains a single-point homozygous deletion (p16) flanked by SNPs that show no copy number alterations (Table 1). These two examples illustrate that the method may be used to detect amplification or deletion at single point resolution, and may be used to delineate boundaries between genomic regions that are present at different copy numbers.

While probe sequences on the Mapping 10K Array may be selected specifically for SNP genotyping by allele-specific hybridization, they may not be optimized with regard to high sensitivity and specificity for copy number alterations. However, greater than 96% of the X chromosome SNPs have a correlation greater than 0.85 between log (signal intensity) and log (copy number). In another embodiment an array may be designed with probes that are optimized for estimation of copy number alterations.

Meta-Analysis

In some embodiments the method is used to detect homozygous deletions and amplifications with large copy

TABLE 1

| Marker\ | c-myc region on Chromosome 8 | | | | | |
|---|---|---|---|---|---|---|
| | SNP 55150 (300 kb distal) | | | SNP 511315 (196 kb distal) | | |
| Sample | $^1 2^{\Delta Ct+1}$ | $^2$WGSA | $^3$Sig | $2^{\Delta Ct+1}$ | WGSA | Sig |
| SK-BR-3 | 32.00 | 14.88 | <−20 | 22.63 | 19.53 | −11.89 |
| MCF-7 | 9.19 | 4.51 | −3.47 | 7.46 | 6.12 | −1.89 |
| ZR-75-30 | 13.00 | 7.41 | −7.67 | 11.31 | 15.27 | −9.95 |
| Hs578 Bst | 2.60 | 2.59 | −0.86 | 2.64 | 3.24 | −0.77 |
| Marker\ | P16 region on Chromosome 9 | | | | | | | | |
| | SNP 827951 (235 kb proximal) | | | SNP 139369 (inside p16) | | | SNP 87445 (21 kb distal) | | |
| Sample | $2^{\Delta Ct+1}$ | WGSA | Sig | $2^{\Delta Ct+1}$ | WGSA | Sig | $2^{\Delta Ct+1}$ | WGSA | Sig |
| BT-20 | 1.82 | 1.99 | −0.31 | 0.008 | 0.26 | −12.06 | 1.32 | 1.64 | −0.71 |
| MCF-12A | 1.29 | 1.09 | −1.46 | 0.014 | 0.31 | −10.44 | 0.08 | 0.62 | −8.12 |
| MCF-7 | 1.33 | 1.89 | −0.37 | 0.002 | 0.29 | −10.83 | 1.00 | 1.02 | −2.68 |
| Hs578 Bst | 2.28 | 1.94 | −0.35 | 1.073 | 1.68 | −0.60 | 1.23 | 1.82 | −0.56 |

Note:
[1]$2^{\Delta Ct+1}$: theoretical estimate of copy number using quantitative PCR
[2]WGSA: copy number estimated by WGSA assay
[3]Sig: $\text{Log}_{10}$(p-value). P-value is derived by comparing the target sample to a reference set consisting of normal people number increases. However, the detection rate of regions with small copy number changes is relatively low. In one example, at a 1% false positive rate, the detection rate for 1X, 3X, 4X and 5X samples was 22.03%, 12.35%, 31.27% and 54.86% respectively. This moderate detection rate is due to dispersion of the reference set distribution in some SNPs rather than the lack of dosage response. Overall, the dosage response is strong with a correlation greater than 0.72 between log (intensity) and log (copy number) for all 302 X chromosome SNPs. Furthermore, 292 SNPs (96.7%) among this group have a correlation greater than 0.85. Meta-analysis assumes that the greater the number of consecutive SNPs which display the same type of alteration (gain or loss) leads to increased confidence (Salamon, et al (2000), *Genome Res*, Vol. 10, pp.2044-54.) and is therefore applied to improve the detection rate. Meta-analysis results in a substantial shift of the Receiving Operating Characteristic (ROC) curves toward the upper left corner, indicating highly improved sensitivity and specificity. The results show that with less than 0.2% false positive rate, the true positive (detection) rate for 1X, 4X and 5X are 91.06%, 91.39% and 98.34% respectively. The true positive rate for 3X is improved to more than 50% by using a false positive rate of less than 1%. Meta-analysis shows much stronger power than individual analysis in these X chromosome examples because the span of the changes is continuous and large, and the majority of the SNPs consistently show the same trend towards gain or loss although sporadic individual signals may not be significant due to reference set dispersion.

A comparison of individual analysis and meta-analysis using autosomal SNPs over a range of p-value thresholds is summarized in Table 2.

TABLE 2

| Method | Individual Analysis | | | Meta Analysis | | |
|---|---|---|---|---|---|---|
| Sample P-value | Can 10 Num (%) | Ref 110 Num (%) | Ratio (C/R) | Can 10 Num (%) | Ref 110 Num (%) | Ratio (C/R) |
| <10e-16 | 7.1 (0.07%) | 1.3 (0.01%) | 5.5 | 1533.6 (14.07%) | 2.2 (0.02%) | 697.1 |
| <10e-14 | 10.5 (0.10%) | 1.7 (0.02%) | 6.2 | 1689.0 (15.49%) | 3.8 (0.03%) | 444.5 |
| <10e-12 | 14.9 (0.14%) | 2.2 (0.02%) | 6.8 | 1918.0 (17.59%) | 7.5 (0.07%) | 255.7 |
| <10e-10 | 24.0 (0.22%) | 2.8 (0.03%) | 8.6 | 2193.9 (20.12%) | 14.8 (0.14%) | 148.2 |
| <10e-8 | 36.1 (0.33%) | 4.0 (0.04%) | 9.0 | 2582.1 (23.68%) | 34.7 (0.32%) | 74.4 |
| <10e-6 | 70.6 (0.65%) | 7.1 (0.06%) | 10.0 | 3113.7 (28.56%) | 102.0 (0.94%) | 30.5 |
| <10e-4 | 207.4 (1.90%) | 26.3 (0.24%) | 7.9 | 3965.6 (36.37%) | 356.0 (3.27%) | 11.1 |
| <10e-2 | 1078.1 (9.89%) | 363.3 (3.33%) | 3.0 | 5744.7 (52.69%) | 1798.3 (16.49%) | 3.2 |

For a given p-value cut-off, the average number of SNPs detected in the 10 breast cancer samples was divided by the average number of SNPs detected in the 110 normal samples. This value serves as an approximate cancer sample to normal sample ratio (signal to noise ratio) for any given confidence threshold. Using meta-analysis, this ratio is substantially improved: for an arbitrary p-value cut-off of $10^{-10}$, with ratios of 8.6 and 148.2 for individual and meta-analysis respectively. This high signal to noise ratio also implies that the number of genomic alterations that span large regions with sufficient SNP density is relatively frequent in the cancer cell lines while relatively rare in the normal population.

LOH

Matched Hs578 samples were used to compare traditional LOH identification (comparison of WGSA SNP genotype calls between matched samples) with the application of a probability model for LOH identification. The model uses allele frequency information for the reference set and calculates the probability that any given stretch of homozygous genotypes may occur due to random chance. The significance increases as the number of homozygous SNPs in the covered region increases. Thus the use of a stringent significance cut-off may allow genomic regions with many consecutive homozygous calls to serve as a surrogate for conventionally defined regions of LOH. This application may be particularly useful when there is no matched normal control sample available for analysis. The method was evaluated using the matched Hs578 pair as to how well it captures traditionally defined LOH markers. The comparative results are summarized in Table 3.

TABLE 3

| P-value | Normal Match (Percentage) | Tumor Sample (Percentage) |
|---|---|---|
| <10e-8 | 0 (0.00%) | 955 (73.78%) |
| <10e-6 | 0 (0.00%) | 1037 (80.12%) |
| <10e-4 | 81 (0.72%) | 1086 (83.91%) |
| <10e-2 | 1179 (10.52%) | 1158 (89.48%) |
| Total | 11205 (100.00%) | 1293 (100.00%) |

There are in total 1293 autosomal SNPs defined by traditional LOH analysis. These SNPs are heterozygous in the normal control and homozygous in the tumor sample. Among these SNPs, greater than 70% have significance (p-value) less than $10^{-8}$ using the probability model, and greater than 80% have significance of less than $10^{-6}$. Yet approximately 10% of the SNPs have insignificant p-values (>0.01). This indicates that the majority of the traditionally defined LOH SNPs are located in long stretches of homozygous calls, while ~10% of the SNPs reside in regions without many consecutive homozygous calls. In contrast, for all the 11,205 autosomal SNPs in the normal control sample, there are no SNPs which belong to stretches with p-values lower than $10^{-6}$, and less than 1% belong to stretches with a significance level of $10^{-4}$. Thus for this particular sample pair, a p-value threshold of $10^{-6}$ results in greater than 80% capture of the traditionally defined LOH using the probability model, while the normal sample contains no regions at this level of significance. This result shows that the probability model can identify genomic regions that have undergone LOH and can serve as an alternative approach to LOH identification especially when normal matched samples are not available. Copy number analysis of SNPs undergoing LOH in the tumor cell line reveals that approximately 32% have one copy, 51% have 2 copies, 17% show moderate amplification (copy number less than 8) and less than 0.2% show homozygous deletions or large fold amplifications. In addition, the copy number distributions are similar between the two approaches use for LOH identification.

Once a homozygous stretch is defined, intensity information may be used to determine the copy number change of the region and its significance. Interestingly, the matched pair identifies regions of LOH where no obvious copy number alterations occur. By comparing the tumor and normal genotype calls, the entire length of chromosome 12 and chromosome 17, as well as ~90 to 170 Mb on chromosome 5, can be defined as LOH, but no significant copy number alterations were observed. This pattern was also observed in MCF-7 where a putative stretch of LOH containing 77 SNPs defined with the probability model from 57 to 77 Mb (p-value 7.2E-16) shows no copy number reduction. Additionally, SK-BR-3 and ZR-75-30 both show a region of putative LOH from 110 to 125-135 Mb with respective p-values of 3.8E-18 (80 SNPs) and 1.8E-24 (120 SNPs) but show significant copy number increases. These examples of LOH with either no copy number reduction or copy number increases may not be readily identified by many currently used single molecular approaches, and underscore the power in coupling LOH measurements with genome wide copy number profiling.

Mixing Experiment

Tumor samples can often be contaminated by normal cells of either stromal or lymphocytic origin. While methods such as laser capture micro dissection or flow cytometry have been successfully used to enrich for tumor cells, the resulting populations rarely are completely pure and thus molecular methods that are used for genome-wide DNA copy number profiling must be robust enough to accommodate heterogeneous samples. The matched pair Hs-578 was used to assess the tolerance of the WGSA assay and the algorithm to mixed DNA samples by testing the effect of increasing amounts of normal DNA (Hs-578Bst) mixed into the cancer sample (Hs-578T). Mixed samples were analyzed for changes in LOH and for changes in the detection of copy number alterations. DNA derived from the cancer cell line was mixed prior to the WGSA assay with the normal matched DNA at increasing percentages of 0% (pure cancer sample), 10%, 20%, 30%, 40%, 50%, 60%, 70%, 80%, 90%, and 100% (pure normal samples). The modal chromosome number of Hs-578Bst and Hs-578T is 46 (diploid) and 59 (hypo triploid) respectively, thus mixing by DNA mass approximates mixing by cell number. Changes in the identification of conventional LOH SNPs were observed as well as putative LOH regions using the probability model. As the contribution of normal DNA increases, the number of traditionally defined LOH SNPs decreases. Following the same trend, the total length and total number of LOH regions defined by the probability model also decrease. Overall, when the percentage of normal DNA is less than or equal to 30%, greater than 70% of the LOH changes are retained. A significant shift occurs when the mixed normal DNA reaches 30 to 50% of the total, resulting in nearly 60% loss of detection of LOH. When normal DNA is present at 60% or greater, most SNPs (>98%) undergoing LOH are undetectable.

The relationship between the transition points of LOH detection and the copy number of these SNPs was also examined. This comparison involves three groups of LOH SNPs with different copy numbers which comprise 99.8% of the total: 1-copy (407 SNPs), 2-copy (663 SNPs), and moderate copy (3 to 8) number increases (221 SNPs). On average, as the percentage of normal DNA increases in the mixed sample, the inability to detect a homozygous call occurs first for SNPs with one copy, followed next by those with two copies, and lastly with those of moderate copy. The difference between the three groups is statistically significant with a p-value 3.292e-05 using the Kruskal Wallis test. The Wilcoxon rank sum test was used to compare each pair. The following p-values for the differences between groups were found: 0.00742 (1-copy and 2-copy), 0.00487 (2-copy and moderate copy), and 1.349e-05 (1-copy and moderate copy). All comparisons are significant at a 0.05 level with Bonferroni correction, with the difference between the 1-copy and the moderate copy groups being the most significant.

The effect of mixed samples on detection of gains and losses was examined as well. The relative percentage of copy number alterations that are detected in mixed samples with meta-analysis is greater than individual SNP analysis. At mixing levels of 10%, 20%, and 30% normal DNA, the detectable signals remaining from the original total are, respectively, 89.01%, 85.65% and 57.55% (meta analysis) and 50%, 25% and 21.43% (individual analysis). Once the proportion of normal DNA reaches 40% of the total sample, there is a significant reduction in the detection of these amplified and deleted SNPs; when the mixed sample contains more than 60% normal DNA, most of the signals are undetectable. This trend is true for both meta-analysis and individual analysis. These results indicate that detection of LOH and copy number alterations using the WGSA assay and algorithm can tolerate a mixed sample containing up to 20 to 30% normal DNA.

Measuring Copy Number Alterations in "Normal" Samples

The reference set of 110 reference samples was also analyzed to determine if amplifications or deletions could be identified within genomic regions in individuals that have not been diagnosed with cancer. More specifically, leave-one-out analysis was done on each of the 110 samples: one sample was left out of the analysis and the other 109 samples were used to build the reference distribution and calculate each SNP's allele frequency. The "left-out" sample was compared with the reference information to evaluate the frequency and significance of copy number alteration and to identify long stretches of homozygous calls in the left-out sample. The results showed that a substantial proportion of the reference samples have significant copy number alteration and long stretches of homozygous calls. Among the 110 samples, 43 have more than 10 single point alterations with p-value less than $10^{-6}$, among them 11 samples have 20 or more such significant alterations. Also among the 110 samples, 8 samples were observed to have long homozygous stretches with p-value less than $10^{-10}$, such long stretches of homozygous calls have an average span of 21.36 Mb.

Example of WGSA: Genomic DNA was digested with XbaI by mixing 5 µl 50 ng/µl human genomic DNA (Coriell Cell Repositories) with 10.5 µl H$_2$O (Accugene), 2 µl 10× RE buffer 2 (NEB, Beverly, Mass.), 2 µl 10×BSA (NEB, Beverly, Mass.), and 0.5 µl XbaI (NEB, Beverly, Mass.). The reaction was incubated at 30° C. for 2 hours, then the enzyme was inactivated by incubation at 70° C. for 20 min and then to 4° C. The reaction may be stored at −20° C.

For ligation of the adapters the digested DNA was then mixed with 1.25 µl 5 uM adaptor in TE pH 8.0, 2.5 µl T4 DNA ligation buffer and 1.25 µl T4 DNA Ligase (NEB, Beverly, Mass.) which is added last. The reaction was incubated at 16° C. for 2 hours then at 70° C. for 20 min and then to 4° C. The 25 µl ligation mixture is then diluted with 75 µl H$_2$O and may be stored at −20° C.

For PCR 10 µl of the diluted ligated DNA is mixed with 10 µl PCR buffer II (Perkin Elmer, Boston, Mass.), 10 µl 2.5 mM dNTP (PanVera Takara, Madison, Wis.), 10 µl 25 mM MgCl$_2$, 7.5 µl 10 µM primer (for a final concentration of 0.75 µM), 2 µl 5U/µl Taq Gold (Perkin Elmer, Boston, Mass.) and 50.5 µl H$_2$O. For each array four 10 µl reactions were prepared. Amplification was done using the following program: 95° C. for 3 min; 35 cycles of 95° C. for 20 sec, 59° C. for 15 sec and 72° C. for 15 sec; and a final incubation at 72° C. for 7 min. The reactions were then held at 4° C. The lid heating option was selected.

The PCR reactions were then purified by mixing the 100 µl PCR reaction with 500 µl PB or PM buffer into Qiagen columns (Valencia, Calif.) and the column was centrifuged at 13,000 rpm for 1 min. Flow through was discarded and 750 µl PE buffer with ethanol was added into the column to wash the sample and the column was spun at 13,000 rpm for 1 min. The flow through was discarded and the column was spun at 13,000 rpm for another 1 min. The flow through was discarded and the column was placed in a new collection tube. For 2 of the 4 samples 30 μl of EB elution buffer pH 8.5 was added to the center of the QIAquick membrane to elute the sample and the columns were allowed to stand at room temperature for 5 min and then centrifuged at 13,000 for 1 min. The elution buffer from the first 2 samples was then used to elute the other 2 samples and the eluates were combined. The DNA was quantified and diluted so that 48 μl contains 20 μg DNA.

The DNA was fragmented by mixing 48 μl DNA (20 μg), 5 μl RE Buffer 4, and 2 μl 0.09 U/μl DNase in a total volume of 55 μl. The reaction was incubated at 37° C. for 30 min then 95° C. for 15 min and then held at 4° C.

Fragments were labeled by incubating 50 μl fragmented DNA, 13 μl 5× TdT buffer (Promega, Madison, Wis.), 1 μl 1 mM biotinolated-ddATP (NEN Life Sciences, Boston, Mass.), and 1 μl TdT (Promega, Madison, Wis.) at 37° C. overnight then at 95° C. for 10 min, then held at 4° C.

Hybridization mix is 12 μl 1.22 M MES, 13 μl DMSO, 13 μl 50× Denharts, 3 μl 0.5M EDTA, 3 μl 10 mg/ml herring sperm DNA, 3 μl 10 nM oligo B2, 3 μl mg/ml Human Cot-1,3 μl 1% Tween-20, and 140 μl 5M TMACL. 70 μl labeled DNA was mixed with 190 μl hybridization mix. The mixture was incubated at 95° C. for 10 min, spun briefly and held at 47.5° C. 200 μl of the denatured mixture was hybridized to an array at 47.5° C. for 16 to 18 hours at 60 rpm.

Staining mix was 990 μl $H_2O$, 450 μl 20×SSPE, 15 μl Tween-20, 30 μl 50% Denharts. For the first stain mix 495 μl staining mix with 51 μl mg/ml streptavidin (Pierce Scientific, Rockford, Ill.), for the second stain mix 495 μl staining mix with 5 μl 0.5 mg/ml biotinylated anti-streptavidin antibody (Vector Labs, Burlingame, Calif.) and for the third stain mix 495 μl staining mix with 5 μl 1 mg/ml streptavidin, R-phycoerythrin conjugate (Molecular Probes, Eugene, Oreg.). Wash and stain under standard conditions.

CONCLUSION

Methods of identifying changes in genomic DNA copy number are disclosed. Methods for identifying loss of heterozygosity, homozygous deletions and gene amplifications are disclosed. The methods may be used to detect copy number changes in cancerous tissue compared to normal tissue. A method to identify genome wide copy number gains and losses by hybridization to a genotyping array comprising probes for more than 10,000 human SNPs is disclosed. Copy number estimations across the genome are linked to SNP genotype calls (LOH analysis). All cited references are incorporated herein by reference for all purposes.

The present inventions provide methods and computer software products for estimating copy number in genomic samples. It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring signal intensity resulting from genomic DNA could be used. The scope of the invention should, therefore, be determined not with reference to the above description, but should instead be determined with reference to the appended claims, along with the full scope of equivalents to which such claims are entitled.

What is claimed is:

1. A method for estimating the copy number of a genomic region in an experimental sample comprising:

(a) isolating nucleic acid from the experimental sample;

(b) amplifying at least some regions of the nucleic acid;

(c) labeling the amplified products;

(d) hybridizing the labeled amplified products to an array to obtain a hybridization pattern, wherein the array comprises a plurality of genotyping probe sets for a plurality of SNPs comprising autosomal SNPs, wherein a probe set comprises:

(i) a plurality of perfect match probes to a first allele of a SNP, (ii) a plurality of perfect match probes to a second allele of the SNP, (iii) a plurality of mismatch probes to the first allele of the SNP, and (iv) a plurality of mismatch probes to the second allele of the SNP, (e) obtaining a measurement for the SNP in the experimental sample wherein the measurement, S, is the log of the arithmetic average of the intensities of at least two of the perfect match probes to said first allele or at least two of the perfect match probes to said second allele for the SNP in the hybridization pattern normalized to the S values of all SNPs genotyped in the experimental sample;

(f) obtaining an S value for the SNP in each of a plurality of reference samples that are matched to the experimental sample in genotype call at the SNP, wherein the S value is the log of the average of the intensities of at least two perfect match probes in a reference hybridization pattern normalized to the S values of all SNPs genotyped in that reference sample;

(g) calculating the mean for the reference sample S values using the values obtained in (f);

(h) obtaining a log intensity difference by subtracting the mean value obtained in (g) from the value of the measurement, S, obtained in (e); and (i) estimating the copy number of the region including the SNP wherein copy number is estimated using:

$$\text{Copy Number} \approx \exp(b + m \times (\tilde{S}_{jg}^{C} - \hat{\mu}_{jg}))$$

wherein $S_{jg}^{C}$ is the log of the average of the intensities of the perfect match probes for a SNP j of genotype g in an experimental sample c, normalized to the S values of all SNPs genotyped in the experimental sample, $\hat{\mu}_{jg}$ is the mean of the S values for SNP j in a plurality of reference samples of genotype g at SNP j, b is the y-intercept and m is the slope of a line defined by plotting intensity values from SNPs of known copy number and obtaining from the estimated copy number an estimated copy number alteration and an estimated direction of copy number change.

2. The method of claim 1 wherein the S values for all SNPs genotyped in the experimental sample and in each reference sample are normalized so that the mean of the S values for all the autosomal SNPs in a sample is zero and the variance is 1.

3. The method of claim 1 further comprising calculating a p-value for the estimated copy number alteration and determining if the p-value is less than a threshold p-value, wherein the estimated direction of copy number change is significant if the p-value is less than the threshold.

4. The method of claim 2 further comprising calculating a p-value for the estimated copy number alteration and determining if the p-value is less than a threshold p-value, wherein the estimated direction of copy number change is significant if the p-value is less than the threshold.

5. The method of claim 1 wherein the S value is calculated using:

$$S = \text{Log}\left(\frac{1}{X}\sum_{i=1}^{X} PM_i\right)$$

where $PM_i$ is the intensity of the perfect match cell of probe pair i and X is the number of perfect match probes in a set.

6. The method of claim 5 wherein X is between 1 and 30.

7. The method of claim 5 wherein X is 20.

8. The method of claim 1 wherein b is about 0.693 and m is about 0.895.

9. The method of claim 1 wherein the experimental sample is a tumor sample.

10. The method of claim 1 wherein the experimental sample is a mixture of tumor and normal cells.

11. The method of claim 1 wherein the experimental sample is a sample that is from a non-cancerous sample.

12. The method of claim 1 wherein the experimental sample is a sample that is suspected of having a chromosomal anomaly selected from the group consisting of a constitutional anomoly, an acquired anomoly, a numerical anomoly, a structural anomoly and mosaicism.

13. The method of claim 1 wherein at least some of the SNPs of known copy number are SNPs on the X chromosome.

14. The method of claim 1 wherein each S value obtained in (f) that is more than 3 standard deviations from the mean of the S values is excluded from the estimation of mean and standard deviation of the reference distribution calculated in (g).

15. The method of claim 1 wherein a second estimate of copy number is obtained by comparing the discrimination ratio, DR, of a SNP in an experimental sample with an average DR from that SNP in a plurality of genotype matched reference samples, where the DR for a probe set with 20 PM/MM probe pairs is calculated using:

$$DR = \frac{1}{20}\sum_{i=1}^{20}\left(\frac{PM_i - MM_i}{PM_i + MM_i}\right)$$

where $PM_i$ is the intensity of the perfect match cell of probe pair i and $MM_i$ is the intensity of the mismatch cell of probe pair i.

16. A method of identifying a genomic region that is amplified or deleted in an experimental sample comprising:
hybridizing a nucleic acid sample derived from the experimental sample to a genotyping array and measuring hybridization intensities for a plurality of perfect match probes, $PM_i$, where $PM_i$ is the hybridization intensity of the perfect match probe of probe pair i;
calculating a value, S, for each SNP genotyped by the array in the experimental sample using:

$$S = \text{Log}\left(\frac{1}{X}\sum_{i=1}^{X} PM_i\right)$$

where X is the number of PM probes for an individual SNP;
normalizing a plurality of S values calculated for SNPs genotyped in the experimental sample so that the mean of the S values is zero and the variance is one to obtain a plurality of normalized S values for said experimental sample;
obtaining normalized S values for each SNP genotyped by the array in a plurality of reference samples and calculating an average of the normalized S values for each SNP in said plurality of reference samples matched in genotype at that SNP;
estimating copy number of at least one SNP in the experimental sample to obtain an estimated copy number wherein copy number is estimated using:

$$\text{Copy Number} \approx \exp(b + m \times (\tilde{S}_{jg}^{C} - \hat{\mu}_{jg}))$$

wherein $\mathbf{S}_{jg}^{C}$ is the log of the average of the intensities of the perfect match probes for a SNP j of genotype g in an experimental sample c, normalized to the S values of all SNPs genotyped in the experimental sample, $\hat{\mu}_{jg}$ is the average of the normalized S values for SNP j in a plurality of reference samples of genotype g at SNP j, b is the y-intercept and mm is the slope of a line defined by plotting intensity values from SNPs of known copy number;
determining a direction of copy number change for the SNP in the experimental sample by comparing the estimated copy number of the SNP in the experimental sample to the copy number of the SNP in a sample of known copy number at the SNP; and
measuring a p-value to determine confidence level in the predicted direction of change.

17. The method of claim 16 where b is about 0.693 and m is about 0.895.

18. The method of claim 16 wherein the nucleic acid sample is derived from the experimental sample using the whole genome sampling assay (WGSA).

19. A method for estimating the copy number of a region of loss of heterozygosity comprising identifying a region of loss of heterozygosity in an experimental sample by:
(i) identifying at least one contiguous stretch of homozygous SNP genotype calls in the genome of the experimental sample;
(ii) obtaining a probability, $\hat{P}_i$, of homozygosity for each SNP in the contiguous stretch wherein $$\hat{P}_i = \frac{\text{\# of AA or BB calls on } SNPi}{\text{total \# of genotype calls on } SNPi};$$

wherein the SNP has a first allele, A, and a second allele, B, and wherein AA is a homozygous call for the A allele and BB is a homozygous call for the B allele;
(iii) calculating the probability that each of the SNPs in the contiguous stretch is homozygous by using:

$$\hat{P}(SNP\ m\ \text{to}\ n\ \text{homozygous}) = \prod_{i=m}^{n} \hat{P}_i;$$

and,
(iv) identifying the region containing the SNPs as a region of loss of heterozygosity if $\hat{P}$ (SNP m to n homozygous) is less than a p-value threshold; and
estimating the copy number of a region identified as a region of loss of heterozygosity in (iv) by a method comprising:

calculating a normalized S value for at least one SNP in the identified region of loss of heterozygosity in the experimental sample using:

$$S = \text{Log}\left(\frac{1}{X}\sum_{i=1}^{X} PM_i\right)$$

where $PM_i$ is the intensity of the perfect match cell of probe pair i and X is the number of probe pairs in a set and normalizing the S value;

calculating normalized S values for the at least one SNP from a plurality of matched genotpye call reference samples and calculating an average of the reference sample normalized S values for the SNP;

comparing the normalized S value for the SNP in the experimental sample with the average of the reference sample normalized S values for the SNP to obtain a ratio; and estimating copy number of the SNP in the experimental sample using the ratio and outputting the estimated copy number of the SNP to a display.

20. The method of claim 19 wherein copy number is estimated for 2 or more contiguous SNPs in the region.

21. The method of claim 19 wherein the plurality of matched genotype reference samples comprises at least 10 samples.

22. A computer software product comprising:

computer program code for inputting a plurality of perfect match intensity values ($PM_i$) for each of a plurality of SNPs in each of a plurality of samples comprising an experimental sample and a plurality of reference samples;

computer program code for calculating an experimental S value for each SNP in the experimental sample, wherein said experimental S value is the log of the mean of the perfect match intensity values for that SNP in the experimental sample;

computer program code for calculating a normalized experimental S value for each experimental S value, by normalizing each experimental S value calculated to all of the experimental S values;

computer program code for calculating a reference S value for each SNP in each of a plurality of reference samples, wherein said reference S value is the log of the mean of the perfect match intensity values for that SNP in that reference sample;

computer program code for calculating a normalized reference S value for each reference S value by normalizing that reference S value to all of the reference S values for SNPs in that reference sample to generate normalized S values for each of the reference samples;

computer program code for calculating an average of the normalized reference S values for each individual SNP in all reference samples of matched genotype call at that individual SNP;

computer program code for calculating a difference between the normalized experimental S value of a SNP from an experimental sample and the mean of the normalized reference S values for that SNP in a plurality of reference samples having a genotype matched to the experimental sample at that SNP;

computer program code for estimating the copy number of the SNP using:

$$\text{Copy Number} \approx \exp(b + m \times (\tilde{S}_{jg}^{C} - \hat{\mu}_{jg}))$$

wherein $\mathbf{S}_{jg}^{C}$ is the normalized experimental S value for a SNP j of genotype g in an experimental sample c, $\hat{\mu}_{jg}$ is the mean of the normalized reference S values for SNP j in a plurality of reference samples of genotype g at SNP j, b is the y-intercept and m is the slope of a line defined by plotting S values from SNPs of known copy number;

computer program code for calculating a p-value for a direction of change wherein said direction of change is determined by comparing the copy number of the SNP in a normal reference sample to the estimated copy number of the SNP;

computer program code for determining if the calculated p-value is less than a selected threshold value;

computer program code for outputting the estimated copy number of the SNP to a display; and computer readable media for storing said computer program codes.

23. The computer software product of claim 22 wherein the log of the mean intensity value for each SNP is calculated using $$S = \text{Log}\left(\frac{1}{X}\sum_{i=1}^{X} PM_i\right)$$

where X is the number of PM probes per SNP.

* * * * *